United States Patent
Scott et al.

(10) Patent No.: US 9,545,459 B2
(45) Date of Patent: Jan. 17, 2017

(54) CONTAINER FOR SURGICAL INSTRUMENTS AND SYSTEM INCLUDING SAME

(75) Inventors: Kurt A. Scott, Warsaw, IN (US); Kyle S. Moore, Acushnet, MA (US); Jason T. Sherman, Warsaw, IN (US)

(73) Assignee: DEPUY IRELAND UNLIMITED COMPANY, Co Cork (IE)

( * ) Notice: Subject to any disclaimer, the term of this patent is extended or adjusted under 35 U.S.C. 154(b) by 1154 days.

(21) Appl. No.: 13/436,858

(22) Filed: Mar. 31, 2012

(65) Prior Publication Data
US 2013/0256167 A1    Oct. 3, 2013

(51) Int. Cl.
| | | |
|---|---|---|
| B65D 83/10 | (2006.01) | |
| A61L 2/26 | (2006.01) | |
| A61B 17/15 | (2006.01) | |
| A61F 2/38 | (2006.01) | |
| A61B 17/00 | (2006.01) | |
| A61F 2/46 | (2006.01) | |

(52) U.S. Cl.
CPC .................. *A61L 2/26* (2013.01); *A61B 50/30* (2016.02); *A61B 17/154* (2013.01); *A61B 2017/00199* (2013.01); *A61B 2050/005* (2016.02); *A61B 2050/0082* (2016.02); *A61B 2090/064* (2016.02); *A61B 2090/0807* (2016.02); *A61B 2090/0813* (2016.02); *A61F 2/389* (2013.01); *A61F 2002/4661* (2013.01); *A61F 2002/4666* (2013.01); *A61L 2202/182* (2013.01); *A61L 2202/24* (2013.01)

(58) Field of Classification Search
CPC ...... A61B 17/155; A61B 19/0271; A61L 2/26
USPC ........ 206/363, 370, 576, 320, 701; 220/360, 220/361, 366.1, 367.1, 373; 606/88, 90
See application file for complete search history.

(56) References Cited

U.S. PATENT DOCUMENTS

| | | | | |
|---|---|---|---|---|
| 4,058,214 A | * | 11/1977 | Mancuso | A47J 47/02 206/545 |
| 4,501,266 A | | 2/1985 | McDaniel | |
| 4,512,497 A | * | 4/1985 | Grusin | A47J 47/02 126/389.1 |
| 4,566,448 A | | 1/1986 | Rohr | |

(Continued)

FOREIGN PATENT DOCUMENTS

| | | |
|---|---|---|
| DE | 857860 C | 12/1952 |
| DE | 10335410 A1 | 2/2005 |

(Continued)

OTHER PUBLICATIONS

European Search Report for Eureopean Patent Application No. 06251808.Sep. 2310, dated Jul. 14, 2006, 7 pgs.

(Continued)

*Primary Examiner* — Jacob K Ackun
*Assistant Examiner* — Jenine Pagan
(74) *Attorney, Agent, or Firm* — Barnes & Thornburg LLP

(57) ABSTRACT

A system for use in an orthopedic surgical procedure including a container for orthopedic surgical instruments. The container includes a first shell, and a second shell configured to be coupled to the first shell to define a chamber therein. The second shell is configured to be coupled to the first shell in a plurality of orientations including a first orientation in which fluid is permitted to advance into and out of the chamber, and a second orientation in fluid is prevented from advancing into and out of the chamber.

21 Claims, 18 Drawing Sheets

(56) References Cited

U.S. PATENT DOCUMENTS

| | | | |
|---|---|---|---|
| 4,576,309 A | 3/1986 | Tzifkansky et al. | |
| 4,600,117 A * | 7/1986 | Tzifkansky | A47G 19/26 |
| | | | 220/360 |
| 4,671,943 A * | 6/1987 | Wahlquist | A61L 2/26 |
| | | | 206/363 |
| 4,676,377 A * | 6/1987 | Rainin | B01L 3/021 |
| | | | 206/468 |
| 4,774,063 A * | 9/1988 | Runnells | A61L 2/26 |
| | | | 220/324 |
| 4,795,473 A | 1/1989 | Grimes | |
| 4,796,610 A | 1/1989 | Cromartie | |
| 4,804,000 A | 2/1989 | Lamb | |
| 4,808,186 A | 2/1989 | Smith | |
| 4,822,362 A | 4/1989 | Walker | |
| 4,825,857 A | 5/1989 | Kenna | |
| 4,828,562 A | 5/1989 | Kenna | |
| 4,834,057 A | 5/1989 | McLeod | |
| 4,856,993 A | 8/1989 | Maness et al. | |
| 4,888,021 A | 12/1989 | Forte | |
| 4,892,093 A | 1/1990 | Zarnowski | |
| 4,892,546 A | 1/1990 | Kotz | |
| 4,899,761 A | 2/1990 | Brown et al. | |
| 4,907,578 A | 3/1990 | Petersen | |
| 4,926,847 A | 5/1990 | Luckman | |
| 4,932,974 A | 6/1990 | Pappas | |
| 4,935,023 A | 6/1990 | Whiteside | |
| 4,936,853 A | 6/1990 | Fabian et al. | |
| 4,938,762 A | 7/1990 | Wehrli | |
| 4,944,756 A | 7/1990 | Kenna | |
| 4,959,071 A | 9/1990 | Brown | |
| 4,963,153 A | 10/1990 | Noesberger | |
| 4,973,331 A | 11/1990 | Pursley et al. | |
| 4,979,949 A | 12/1990 | Matsen et al. | |
| 4,986,281 A | 1/1991 | Preves et al. | |
| 5,002,547 A | 3/1991 | Poggie et al. | |
| 5,018,514 A | 5/1991 | Grood et al. | |
| 5,020,797 A | 6/1991 | Burns | |
| 5,032,132 A | 7/1991 | Matsen | |
| 5,033,291 A | 7/1991 | Podoloff et al. | |
| 5,037,423 A | 8/1991 | Kenna | |
| 5,056,530 A | 10/1991 | Butler et al. | |
| 5,080,675 A | 1/1992 | Lawes et al. | |
| 5,082,003 A | 1/1992 | Lamb et al. | |
| 5,084,251 A * | 1/1992 | Thomas | A61B 19/34 |
| | | | 206/557 |
| 5,098,436 A | 3/1992 | Ferrante et al. | |
| 5,122,144 A | 6/1992 | Bert | |
| 5,125,408 A | 6/1992 | Basser | |
| 5,129,909 A | 7/1992 | Sutherland | |
| 5,133,660 A | 7/1992 | Fenick | |
| 5,197,488 A | 3/1993 | Kovacevic | |
| 5,207,711 A | 5/1993 | Caspari et al. | |
| 5,213,112 A | 5/1993 | Niwa | |
| 5,228,459 A | 7/1993 | Caspari et al. | |
| 5,234,433 A | 8/1993 | Bert | |
| 5,234,434 A | 8/1993 | Goble | |
| 5,234,435 A | 8/1993 | Seagrave | |
| 5,236,432 A | 8/1993 | Matsen et al. | |
| 5,250,050 A | 10/1993 | Poggie et al. | |
| 5,257,996 A | 11/1993 | McGuire | |
| 5,281,400 A * | 1/1994 | Berry, Jr. | A61L 2/26 |
| | | | 206/363 |
| 5,312,411 A | 5/1994 | Steele et al. | |
| 5,320,529 A | 6/1994 | Pompa | |
| 5,326,363 A | 7/1994 | Aikins | |
| 5,329,933 A | 7/1994 | Graf | |
| 5,342,367 A | 8/1994 | Ferrante et al. | |
| 5,358,527 A | 10/1994 | Forte | |
| 5,360,016 A | 11/1994 | Kovacevic | |
| 5,364,401 A | 11/1994 | Ferrante | |
| 5,364,402 A | 11/1994 | Mumme | |
| 5,388,714 A * | 2/1995 | Zutler | A61L 9/12 |
| | | | 220/360 |
| 5,395,401 A | 3/1995 | Bahler | |
| 5,403,319 A | 4/1995 | Matsen et al. | |
| 5,417,694 A | 5/1995 | Marik et al. | |
| 5,425,775 A | 6/1995 | Kovacevic et al. | |
| 5,431,652 A | 7/1995 | Shimamoto et al. | |
| 5,431,653 A | 7/1995 | Callaway | |
| 5,443,518 A | 8/1995 | Insall | |
| 5,456,724 A | 10/1995 | Yen et al. | |
| 5,470,354 A | 11/1995 | Hershberger | |
| 5,489,311 A | 2/1996 | Cipolletti | |
| 5,496,352 A | 3/1996 | Renger | |
| 5,514,144 A | 5/1996 | Bolton | |
| 5,514,183 A | 5/1996 | Epstein | |
| 5,520,695 A | 5/1996 | Luckman | |
| 5,540,696 A | 7/1996 | Booth et al. | |
| 5,562,674 A | 10/1996 | Stalcup et al. | |
| 5,569,261 A | 10/1996 | Marik et al. | |
| 5,571,110 A | 11/1996 | Matsen et al. | |
| 5,571,197 A | 11/1996 | Insall | |
| 5,597,379 A | 1/1997 | Haines | |
| 5,611,774 A | 3/1997 | Postelmans | |
| 5,613,971 A | 3/1997 | Lower | |
| 5,630,820 A | 5/1997 | Todd | |
| 5,643,272 A | 7/1997 | Haines | |
| 5,649,929 A | 7/1997 | Callaway | |
| 5,656,785 A | 8/1997 | Trainor et al. | |
| 5,658,293 A | 8/1997 | Vanlaningham | |
| 5,669,914 A | 9/1997 | Eckhoff | |
| 5,671,695 A | 9/1997 | Schroeder | |
| 5,682,886 A | 11/1997 | Delp et al. | |
| 5,683,397 A | 11/1997 | Vendrely et al. | |
| 5,688,280 A | 11/1997 | Booth, Jr. et al. | |
| 5,688,282 A | 11/1997 | Baron et al. | |
| 5,690,635 A | 11/1997 | Matsen et al. | |
| 5,702,422 A | 12/1997 | Stone | |
| 5,702,463 A | 12/1997 | Pothier et al. | |
| 5,733,292 A | 3/1998 | Gustilo et al. | |
| 5,735,904 A | 4/1998 | Pappas | |
| 5,743,909 A | 4/1998 | Collette | |
| 5,769,894 A | 6/1998 | Ferragamo | |
| 5,782,925 A | 7/1998 | Collazo et al. | |
| 5,800,438 A | 9/1998 | Tuke | |
| 5,800,552 A | 9/1998 | Forte | |
| 5,810,827 A | 9/1998 | Haines | |
| 5,824,104 A | 10/1998 | Tuke | |
| 5,840,047 A | 11/1998 | Stedham | |
| 5,860,980 A | 1/1999 | Axelson et al. | |
| 5,871,018 A | 2/1999 | Delp et al. | |
| 5,879,389 A | 3/1999 | Koshino | |
| 5,880,976 A | 3/1999 | DiGioia, III et al. | |
| 5,891,150 A | 4/1999 | Chan | |
| 5,911,723 A | 6/1999 | Ashby | |
| 5,931,777 A | 8/1999 | Sava | |
| 5,935,086 A | 8/1999 | Beacon et al. | |
| 6,013,103 A | 1/2000 | Kaufman et al. | |
| 6,019,767 A | 2/2000 | Howell | |
| 6,022,377 A | 2/2000 | Nuelle et al. | |
| 6,034,296 A | 3/2000 | Elvin et al. | |
| 6,051,263 A * | 4/2000 | Gorlich | B65D 81/263 |
| | | | 220/359.1 |
| 6,056,752 A | 5/2000 | Roger | |
| 6,056,754 A | 5/2000 | Haines | |
| 6,056,756 A | 5/2000 | Eng et al. | |
| 6,080,154 A | 6/2000 | Reay-Young et al. | |
| 6,086,592 A | 7/2000 | Rosenberg | |
| 6,096,043 A | 8/2000 | Techiera et al. | |
| 6,102,952 A | 8/2000 | Koshino | |
| 6,113,604 A | 9/2000 | Whittaker et al. | |
| 6,126,692 A | 10/2000 | Robie et al. | |
| 2,616,514 A | 12/2000 | Bar | |
| 6,165,142 A | 12/2000 | Bar | |
| 6,174,294 B1 | 1/2001 | Crabb et al. | |
| 6,210,638 B1 | 4/2001 | Grieco | |
| 6,293,271 B1 * | 9/2001 | Barbour | A47J 27/12 |
| | | | 126/25 R |
| 6,447,448 B1 | 9/2002 | Ishikawa et al. | |
| 6,488,711 B1 | 12/2002 | Grafinger | |
| 6,540,787 B2 | 4/2003 | Biegun et al. | |
| 6,553,681 B2 | 4/2003 | Ekholm, Jr. et al. | |
| 6,575,980 B1 | 6/2003 | Robie et al. | |

(56) References Cited

U.S. PATENT DOCUMENTS

| | | |
|---|---|---|
| 6,589,283 B1 | 7/2003 | Metzger |
| 6,610,096 B2 | 8/2003 | MacDonald |
| 6,632,225 B2 | 10/2003 | Sanford et al. |
| 6,648,896 B2 | 11/2003 | Overes |
| 6,702,821 B2 | 3/2004 | Bonutti |
| 6,706,005 B2 | 3/2004 | Roy et al. |
| 6,758,850 B2 | 7/2004 | Smith et al. |
| 6,770,078 B2 | 8/2004 | Bonutti |
| 6,821,299 B2 | 11/2004 | Kirking et al. |
| 6,827,723 B2 | 12/2004 | Carson |
| 6,856,834 B2 | 2/2005 | Treppo et al. |
| 6,905,513 B1 | 6/2005 | Metzger |
| 6,923,817 B2 | 8/2005 | Carson |
| 6,972,039 B2 | 12/2005 | Metzger et al. |
| 6,984,249 B2 | 1/2006 | Keller |
| 7,104,996 B2 | 9/2006 | Bonutti |
| 7,153,281 B2 | 12/2006 | Holmes |
| 7,232,416 B2 | 6/2007 | Czernicki |
| 7,357,272 B2 * | 4/2008 | Maxwell ............ B65D 43/0208 220/366.1 |
| 7,412,897 B2 | 8/2008 | Crottel et al. |
| 7,559,931 B2 | 7/2009 | Stone |
| 7,575,602 B2 | 8/2009 | Amirouche et al. |
| 7,578,821 B2 | 8/2009 | Fisher et al. |
| 7,615,055 B2 | 11/2009 | DiSilvestro |
| 7,632,283 B2 | 12/2009 | Heldreth |
| 7,794,499 B2 | 9/2010 | Navarro et al. |
| 7,849,751 B2 | 12/2010 | Clark et al. |
| 7,892,236 B1 | 2/2011 | Bonutti |
| 8,118,815 B2 | 2/2012 | Van Der Walt |
| 8,211,041 B2 | 7/2012 | Fisher et al. |
| 2001/0021877 A1 | 9/2001 | Biegun et al. |
| 2002/0029045 A1 | 3/2002 | Bonutti |
| 2002/0052606 A1 | 5/2002 | Bonutti |
| 2002/0133175 A1 | 9/2002 | Carson |
| 2002/0147455 A1 | 10/2002 | Carson |
| 2002/0156480 A1 | 10/2002 | Overes et al. |
| 2003/0028196 A1 | 2/2003 | Bonutti |
| 2003/0069591 A1 | 4/2003 | Carson et al. |
| 2003/0069644 A1 | 4/2003 | Kovacevic et al. |
| 2003/0130665 A1 | 7/2003 | Pinczewski et al. |
| 2003/0139645 A1 | 7/2003 | Adelman |
| 2003/0144669 A1 | 7/2003 | Robinson |
| 2003/0153978 A1 | 8/2003 | Whiteside |
| 2003/0187452 A1 | 10/2003 | Smith et al. |
| 2003/0236472 A1 | 12/2003 | Van Hoeck et al. |
| 2004/0019382 A1 | 1/2004 | Amirouche et al. |
| 2004/0039254 A1 | 2/2004 | Stivoric et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0122441 A1 | 6/2004 | Muratsu |
| 2004/0243148 A1 | 12/2004 | Wasielewski |
| 2005/0010302 A1 | 1/2005 | Dietz et al. |
| 2005/0021044 A1 | 1/2005 | Stone et al. |
| 2005/0038442 A1 | 2/2005 | Freeman |
| 2005/0082305 A1 | 4/2005 | Dais et al. |
| 2005/0085920 A1 | 4/2005 | Williamson |
| 2005/0113846 A1 | 5/2005 | Carson |
| 2005/0149041 A1 | 7/2005 | McGinley et al. |
| 2005/0177169 A1 | 8/2005 | Fisher et al. |
| 2005/0177170 A1 | 8/2005 | Fisher et al. |
| 2005/0177173 A1 | 8/2005 | Aebi et al. |
| 2005/0234332 A1 | 10/2005 | Murphy |
| 2005/0234448 A1 | 10/2005 | McCarthy |
| 2005/0234465 A1 | 10/2005 | McCombs et al. |
| 2005/0234466 A1 | 10/2005 | Stallings |
| 2005/0234468 A1 | 10/2005 | Carson |
| 2005/0251026 A1 | 11/2005 | Stone |
| 2005/0261071 A1 | 11/2005 | Cameron |
| 2005/0267485 A1 | 12/2005 | Cordes et al. |
| 2006/0012736 A1 | 1/2006 | Nishino et al. |
| 2006/0081063 A1 | 4/2006 | Neubauer et al. |
| 2006/0149277 A1 | 7/2006 | Cinquin et al. |
| 2006/0161051 A1 | 7/2006 | Terrill-Grisoni et al. |
| 2006/0224088 A1 | 10/2006 | Roche |
| 2006/0241569 A1 | 10/2006 | DiSilvestro |
| 2006/0271056 A1 | 11/2006 | Terrill-Grisoni et al. |
| 2007/0162142 A1 | 7/2007 | Stone |
| 2007/0219561 A1 | 9/2007 | Lavallee et al. |
| 2007/0233144 A1 | 10/2007 | Lavallee |
| 2007/0239165 A1 | 10/2007 | Amirouche |
| 2007/0244488 A1 | 10/2007 | Metzger et al. |
| 2008/0051892 A1 | 2/2008 | Malandain |
| 2008/0133022 A1 | 6/2008 | Caylor |
| 2008/0306413 A1 | 12/2008 | Crottet et al. |
| 2009/0005708 A1 | 1/2009 | Johanson et al. |
| 2009/0018544 A1 | 1/2009 | Heavener |
| 2009/0099570 A1 | 4/2009 | Paradis et al. |
| 2009/0138019 A1 | 5/2009 | Wasielewski |
| 2009/0138021 A1 | 5/2009 | Colquhoun |
| 2009/0270869 A1 | 10/2009 | Colquhoun et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0326544 A1 | 12/2009 | Chessar et al. |
| 2010/0016705 A1 | 1/2010 | Stone |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0137871 A1 | 6/2010 | Borja |
| 2010/0198275 A1 | 8/2010 | Chana et al. |
| 2010/0217156 A1 | 8/2010 | Fisher et al. |
| 2010/0249658 A1 | 9/2010 | Sherman et al. |
| 2010/0249659 A1 | 9/2010 | Sherman et al. |
| 2010/0249660 A1 | 9/2010 | Sherman et al. |
| 2010/0249777 A1 | 9/2010 | Sherman et al. |
| 2010/0249789 A1 | 9/2010 | Rock et al. |
| 2010/0249790 A1 | 9/2010 | Roche |
| 2010/0249791 A1 | 9/2010 | Roche |
| 2010/0250571 A1 | 9/2010 | Pierce et al. |
| 2011/0251694 A1 | 10/2011 | Wasielewski |

FOREIGN PATENT DOCUMENTS

| | | |
|---|---|---|
| EP | 0645984 | 4/1995 |
| EP | 0720834 B1 | 6/1999 |
| EP | 1129676 | 9/2001 |
| EP | 1245193 | 10/2002 |
| EP | 1348382 A2 | 10/2003 |
| EP | 1402857 A2 | 3/2004 |
| EP | 1645229 | 4/2006 |
| EP | 1707159 B1 | 11/2008 |
| EP | 1814471 B1 | 3/2010 |
| EP | 1402857 B1 | 8/2010 |
| EP | 1915951 B1 | 6/2011 |
| JP | 10192259 A | 7/1998 |
| JP | 2006158722 A | 6/2006 |
| JP | 2007054488 A | 3/2007 |
| WO | 7900739 | 10/1979 |
| WO | WO 93/25157 A1 | 12/1993 |
| WO | 9617552 A1 | 6/1996 |
| WO | 9935972 | 7/1999 |
| WO | 03065949 A2 | 8/2003 |
| WO | 2004008988 A2 | 1/2004 |
| WO | 2005023120 A1 | 3/2005 |
| WO | 2005037671 A2 | 4/2005 |
| WO | 2005089681 A | 9/2005 |
| WO | 2007036694 A1 | 4/2007 |
| WO | 2007036699 | 4/2007 |
| WO | 2010/011978 A1 | 1/2010 |
| WO | 2010022272 A1 | 2/2010 |
| WO | 2010/030809 A1 | 3/2010 |

OTHER PUBLICATIONS

European Search Report for European Patent Application No. 10156105.8—2319, Jun. 15, 2010, 8 pgs.

(56) References Cited

OTHER PUBLICATIONS

European Search Report, European Patent Application No. 13161816.7-1659, Jun. 28, 2013, 6 pages.

* cited by examiner

CONTAINER FOR SURGICAL INSTRUMENTS AND SYSTEM INCLUDING SAME

TECHNICAL FIELD

The present disclosure relates generally to orthopaedic surgical instruments and, more particularly, to containers for surgical instruments used during orthopaedic surgical procedures.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint. To facilitate the replacement of the natural joint with a prosthetic knee joint, orthopaedic surgeons may use a variety of orthopaedic surgical instruments such as, for example, sensors, controllers, reamers, drill guides, and/or other surgical instruments.

Many orthopaedic surgical instruments are cleaned and sterilized for use in a particular orthopaedic surgical procedure. In a typical cleaning or sterilization process, the instruments may be autoclaved. In such a process, the orthopaedic surgical instruments are placed in sterilization packages or containers for cleaning and sterilization. Other orthopaedic surgical instruments are not cleaned and sterilized before use in a particular orthopaedic surgical procedure. Such non-sterile instruments may be placed in a sealed package or container to prevent contamination of the sterilized surgical instruments or the patient.

SUMMARY

According to one aspect of the disclosure, a container for surgical instruments is disclosed. The container includes a first shell and a second shell configured to be coupled to the first shell to define a chamber therebetween. The second shell may be configured to be coupled to the first shell in a plurality of orientations including a first orientation in which the first shell and the second shell cooperate to define a vent that permits fluid to advance into and out of the chamber, and a second orientation in which the first shell and the second shell cooperate to prevent fluid from advancing into and out of the chamber.

In some embodiments, a first passageway may be defined in the first shell, and a second passageway may be defined in the second shell. When the second shell is coupled to the first shell in the first orientation, the first passageway may be aligned with the second passageway to define the vent. When the second shell is coupled to the first shell in the second orientation, the first passageway may be spaced apart from the second passageway.

In some embodiments, the first shell may include a rim that defines an outward-facing opening, an inner wall that extends inwardly from the opening to define a compartment in the first shell, and an outer wall that extends from the rim opposite the inner wall. The first passageway may be a channel defined in the rim that extends through the inner wall and the outer wall.

In some embodiments, the second shell may include an inner wall that is configured to engage the outer wall of the first shell when the second shell is coupled to the first shell. The second passageway may extend through the inner wall of the second shell. In some embodiments, the first shell may include a flange extending outwardly from the outer wall. The second shell may include a flange that is engaged with the flange of the first shell when the second shell is coupled to the first shell. The second passageway may be a channel extending through the inner wall and the flange of the second shell.

Additionally, in some embodiments, the compartment of the first shell may be a first compartment. The second shell may include a rim that defines an outward-facing opening, and an inner wall that extends inwardly from the opening to define a second compartment in the second shell. When the second shell is coupled to the first shell, the inner wall of the second shell may engage the outer wall of the first shell. The first compartment and the second compartment may cooperate to define the chamber.

In some embodiments, the container may also include an indicator configured to indicate a selected orientation of the plurality of orientations of the second shell relative to the first shell. Additionally, in some embodiments, the indicator may include a first arrow defined in the first shell, and a second arrow defined in the second shell. The first arrow and the second arrow may point in a first direction when the second shell is coupled to the first shell in the first orientation. In some embodiments, the first arrow may point in the first direction and the second arrow may point in a second direction opposite the first direction when the second shell is coupled to the first shell in the second orientation.

In some embodiments, when the second shell is coupled to the first shell in the first orientation, the first shell and the second shell may cooperate to define a receptacle sized to receive a first orthopaedic surgical instrument of the orthopaedic surgical instruments. Additionally, in some embodiments, when the second shell is coupled to the first shell in the first orientation, the first shell and the second shell may cooperate to define a second receptacle sized to receive a second orthopaedic surgical instrument of the orthopaedic surgical instruments.

In some embodiments, the vent defined by the first shell and the second shell when the second shell is coupled to the first shell in the first orientation may be a plurality of vents that permit fluid to advance into and out of the chamber.

According to another aspect, a system for use in an orthopaedic surgical procedure is disclosed. The system includes an orthopaedic surgical instrument having a first side and a second side, a first shell defining a first slot sized to receive the first side of the orthopaedic surgical instrument, and a second shell configured to be coupled to the first shell. The second shell defines a second slot sized to receive the second side of the orthopaedic surgical instrument. The second shell is configured to be coupled to the first shell in a plurality of orientations including a first orientation in which the first slot and the second slot cooperate to define a receptacle sized to receive the orthopaedic surgical instrument. When the second shell is coupled to the first shell in the first orientation, fluid is permitted to advance into and out of the receptacle. When the orthopaedic surgical instrument is received in the first slot of the first shell and the second shell is in a second orientation of the plurality of orientations, the second shell is configured to engage the orthopaedic surgical instrument such that the second shell is prevented from being coupled to the first shell in the second orientation.

In some embodiments, the first shell may include a rim that defines an outward-facing opening and an inner wall that extends inwardly from the opening to a base wall. The inner wall and the base wall may define a compartment in the first shell that includes the first slot. Additionally, in some embodiments, the first slot of the first shell may include a first end defined by a first inner surface of the first shell located in an imaginary plane positioned between the rim and the base wall, and a curved surface extending upwardly from the first inner surface. The first slot may include a second end defined by a second inner surface, a third inner surface, and a fourth inner surface. The second inner surface may be located in a second imaginary plane positioned between the rim and the base wall and may extend parallel to the first inner surface. The third inner surface may be located in a third imaginary plane positioned between the rim and the second imaginary plane, and the fourth inner surface may extend obliquely between the second inner surface and the third inner surface.

In some embodiments, the second shell may include a rim that defines an outward-facing opening and an inner wall that extends inwardly from the opening to a base wall. The inner wall and the base wall may define a compartment in the second shell that includes the second slot.

In some embodiments, the second slot of the second shell may include a first end defined by a first inner surface of the second shell. The first inner surface may be located in a fourth imaginary plane positioned between the rim and the base wall of the second shell. Additionally, in some embodiments, the second slot may have a second end defined by a second inner surface, a third inner surface, and a fourth inner surface of the second shell. The second inner surface of the second shell may be located in a fifth imaginary plane positioned between the rim and the base wall of the second shell. The third inner surface may be located in a sixth imaginary plane positioned between the rim of the second shell and the fifth imaginary plane. The fourth inner surface of the second shell may extend obliquely between the second inner surface and the third inner surface of the second shell.

In some embodiments, when the second shell is coupled to the first shell in the first orientation, the first end of the first slot of the first shell and the first end of the second slot of the second shell may be aligned to define a first end of the receptacle, and the second end of the first slot and the second end of the second slot may be aligned to define a second end of the receptacle. When the second shell is coupled to the first shell in the second orientation, the first end of the first slot may be aligned with the second end of the second slot.

In some embodiments, the system may include a second orthopaedic surgical instrument. When the second shell is coupled to the first shell in the second orientation, the first shell and the second shell may cooperate to define a second receptacle sized to receive the second orthopaedic surgical instrument. Additionally, in some embodiments, when the second shell is coupled to the first shell in the second orientation, fluid may be prevented from advancing into and out of the second receptacle.

According to another aspect, the system includes a container. The container includes a first shell including a rim that defines an outward-facing opening, and an inner wall that extends inwardly from the opening to a base wall. The inner wall and the base wall define a first compartment. The first shell includes an outer wall that extends from the rim opposite the inner wall. The container also includes a second shell configured to be coupled to the first shell in a plurality of orientations. The second shell includes a rim that defines an outward-facing opening, an inner wall that extends inwardly from the opening to a base wall. The inner wall and the base wall of the second shell define a second compartment. When the second shell is coupled to the first shell, the inner wall of the second shell engages the outer wall of the first shell, and the first compartment and the second compartment cooperate to define a chamber in the container. The plurality of orientations include a first orientation in which fluid is permitted to advance into and out of the chamber and a second orientation in which fluid is prevented from advancing into and out of the chamber.

In some embodiments, the first shell may include a first passageway that extends through the inner wall and the outer wall of the first shell. When the second shell is coupled to the first shell in the first orientation, the first passageway may be aligned with a second passageway of the second shell to permit fluid to advance into and out of the chamber. In some embodiments, when the second shell is coupled to the first shell in the second orientation, the first passageway may be spaced apart from the second passageway to prevent fluid from advancing into and out of the chamber.

In some embodiments, the inner wall of the second shell may be positioned over the first passageway of the first shell when the second shell is coupled to the first shell in the second orientation. Additionally, in some embodiments, the first passageway may include a first channel defined in the rim of the first shell, and the second passageway may include a second channel defined in the second shell.

In some embodiments, the system may include a first orthopaedic surgical instrument, and a second orthopaedic surgical instrument. When the second shell is coupled to the first shell in the first orientation, the chamber may include a first receptacle sized to receive the first orthopaedic surgical instrument. When the second shell is coupled to the first shell in the second orientation, the chamber may include a second receptacle sized to receive the second orthopaedic surgical instrument.

BRIEF DESCRIPTION OF THE DRAWINGS

The detailed description particularly refers to the following figures, in which.

DETAILED DESCRIPTION OF THE DRAWINGS

Figure 1:
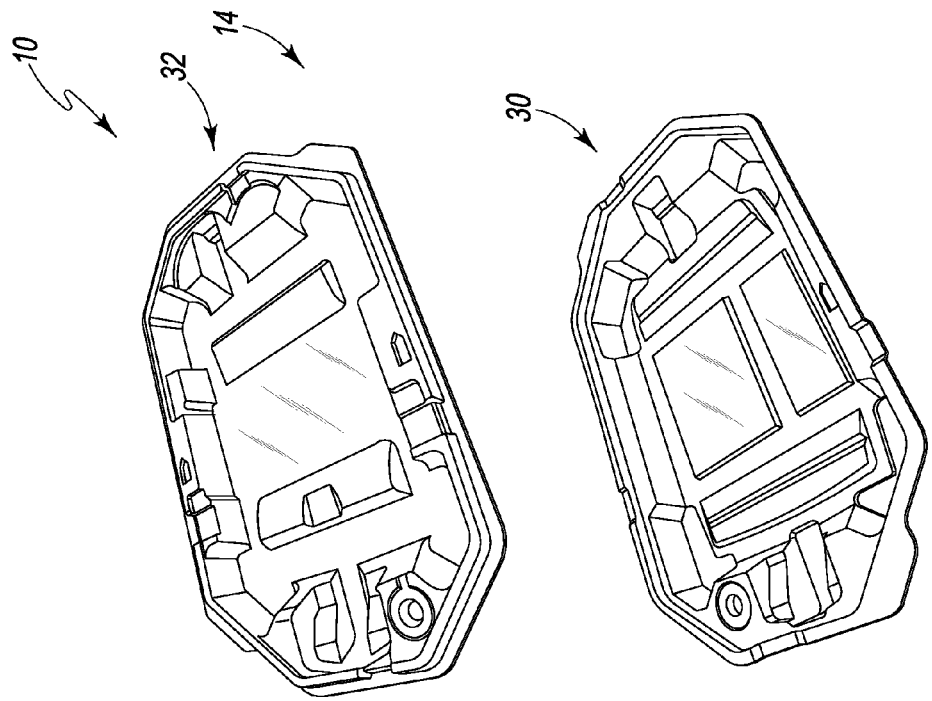
FIG. 1 is an exploded perspective view of an orthopaedic surgical instrument system.
Figure 1:
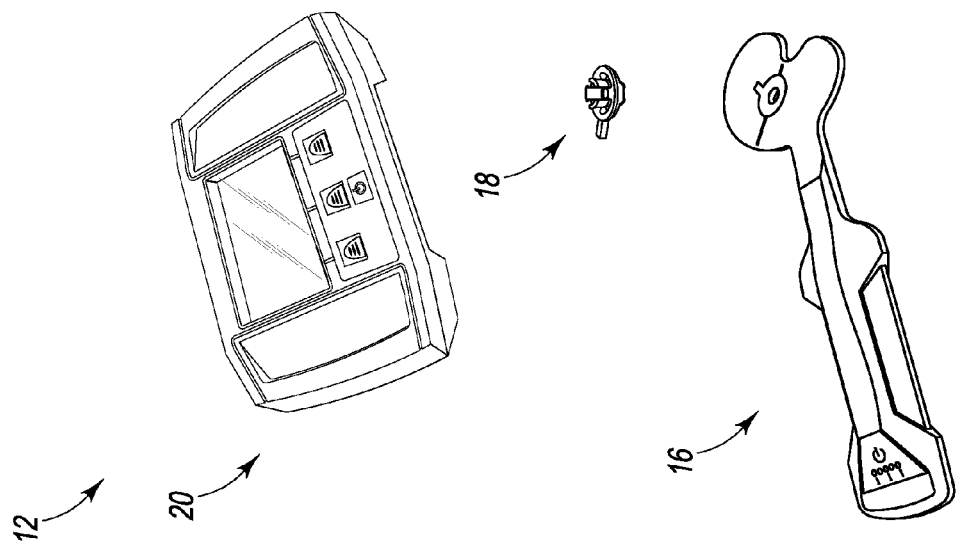

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, a system 10 for use in an orthopaedic surgical procedure includes a plurality of orthopaedic surgical instruments 12 and a surgical instrument container 14 capable of carrying any of the instruments 12. In the illustrative embodiment, the instruments 12 include a sensor module 16, an adaptor 18, and a hand-held display module 20, which may be used to determine and display joint forces of a patient's joint during the orthopaedic surgical procedure. It should be appreciated that in other embodiments the plurality of surgical instruments may include additional or other instruments, such as, for example, reamers, saw blade, prosthetic trails, and so forth. Thus, although the container 14 and the system 10 are described below in regard to instruments for use in one arthroplasty surgical procedure, certain concepts associated with the container 14 and the system 10 may be utilized in replacement procedures of numerous other joints throughout the body.

Figure 2:
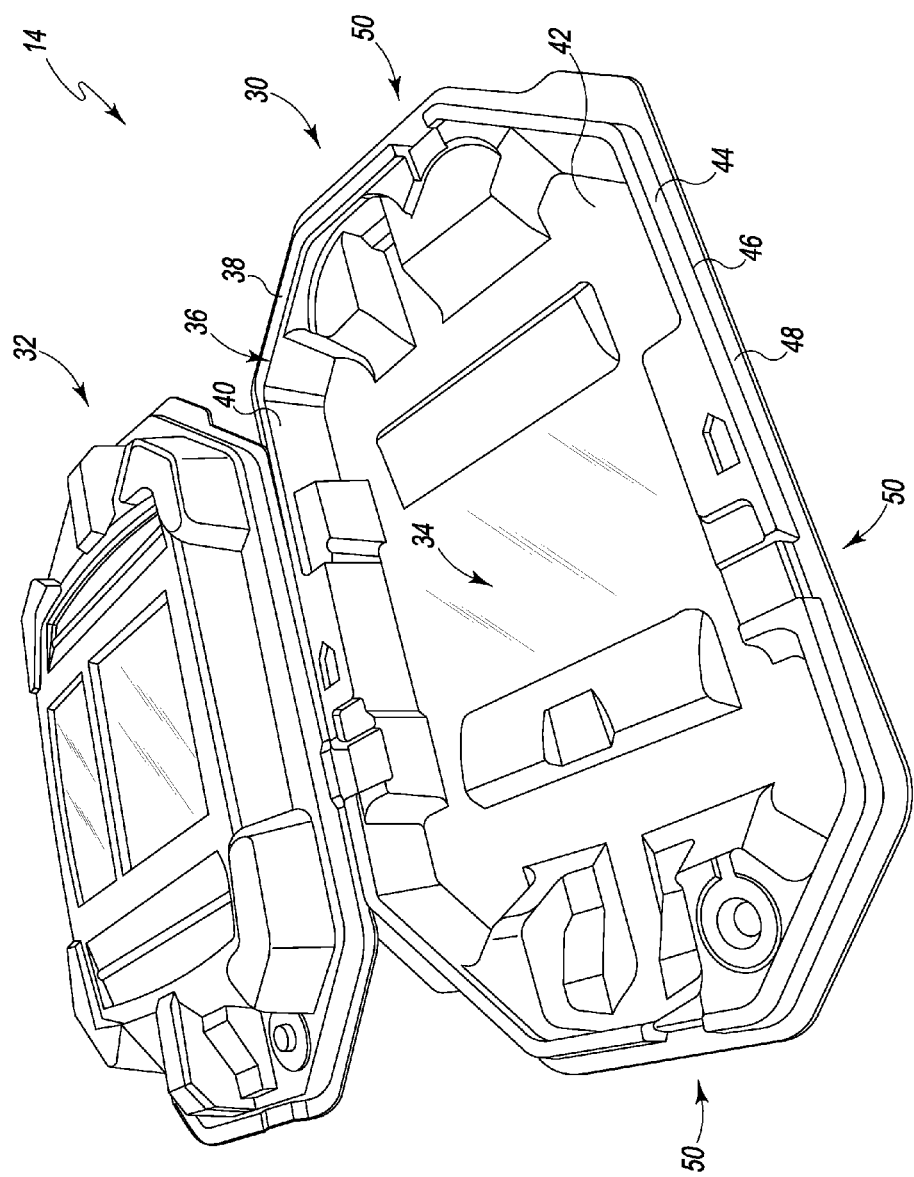
FIG. 2 is a perspective view of a disassembled surgical instrument container of the system of FIG. 1.

As shown in FIG. 2, the container 14 of the system 10 includes a shell 30 and a shell 32 configured to be coupled to the shell 30. For clarity of description, the shells 30, 32 are respectively described below as "a lower shell 30" and "an upper shell 32," and some structures of the shells 30, 32 are described in reference to directions such as, for example, vertical, horizontal, upward, downward, and so forth. However, it should be appreciated that the shells 30, 32 may be flipped or switched such that the shell 30 is the upper shell and the shell 32 is the lower shell. Additionally, the shells 30, 32 may be rotated such that one shell is "a right shell" or "front shell" and the other is "a left shell" or "rear shell."

In the illustrative embodiment, each of the shells 30, 32 is formed from a rigid, transparent plastic that has been molded into the required shape. In other embodiments, the shells may be formed from a plastic that is semi-transparent or opaque. It should also be appreciated that in other embodiments the shells may be formed from another polymeric material or a metallic material such as, for example, aluminum.

The lower shell 30 of the container 14 defines a compartment 34 having an opening 36 that is defined by a rim 38. The lower shell 30 includes an inner wall 40 that extends inwardly from the opening 36 to a base wall 42. The walls 40, 42 cooperate to define the compartment 34. The lower shell 30 also includes an outer wall 44 that extends away from the rim 38 to a lower end 46, and a flange 48 that extends outwardly from the lower end 46 of the outer wall 44. As described in greater detail below, a number of passageways 50 are defined in the lower shell 30, and each passageway 50 is sized to permit fluid, such as, for example, an instrument sterilization gas, to advance into and out of the compartment 34.

Figure 3:
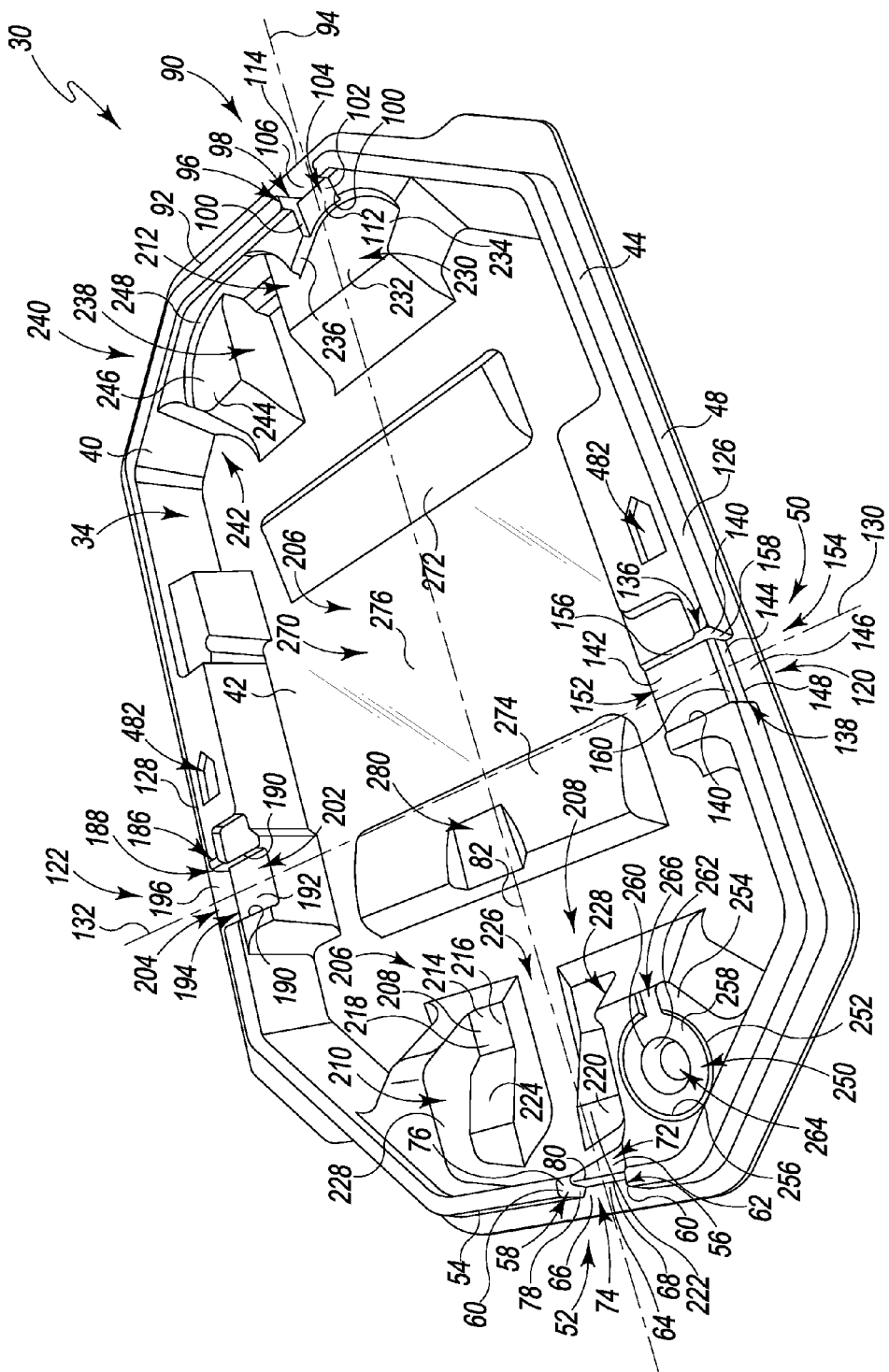
FIG. 3 is a perspective view of a lower shell of the surgical instrument container of FIG. 2.

Referring now to FIG. 3, the passageways 50 of the lower shell 30 include a channel 52 defined in a side 54 of lower shell 30. As shown in FIG. 3, the channel 52 includes a notch 56 defined in the rim 38 and the inner wall 40. The channel 52 also includes an opening 58 defined in the outer wall 44. The channel 52 is defined between a pair of opposing surfaces 60 that extend downwardly from the notch 56 and inwardly from the opening 58 to a pair of walls 62, 64. The channel 52 is further defined by another wall 66 that extends inwardly from the opening 58 to a lower end 68 of the wall 64.

As shown in FIG. 3, the walls 62, 64, 66 cooperate to define a stepped bottom wall of the channel 52 such that the channel 52 is divided into an upper segment 72 and a lower segment 74. Each opposing surface 60 includes a section 76 that extends downwardly from the notch 56 to the wall 62, which is positioned between the rim 38 and the lower end 46 of the outer wall 44. The sections 76 of the surfaces 60 and the wall 62 define the upper segment 72. Each opposing surface 60 also includes a section 78 that extends inwardly from the opening 58 to the wall 64, which extends downwardly from an edge 80 of the wall 62. The sections 78 of the surfaces 60, the wall 64, and the wall 66 define the lower segment 74 of the channel 52. It should be appreciated that in other embodiments the channel may have a substantially planar bottom wall. In other embodiments, the bottom wall of the channel 52 may be angled or sloped.

The channel 52 of the lower shell 30 defines a longitudinal axis 82 and extends through the outer wall 44 and the inner wall 40 to the compartment 34. As shown in FIG. 3, the passageways 50 of the lower shell 30 includes another channel 90 that is defined in the side 92 of the lower shell 30 opposite the side 54. The channel 90 also defines a longitudinal axis 94 and extends through the outer wall 44 and the inner wall 40 to the compartment 34. In the illustrative embodiment, the longitudinal axis 94 is coaxial with the longitudinal axis 82 such that the channels 52, 90 are aligned. It should be appreciated that in other embodiments the axes 82, 94 of the channels 52, 90 may be offset or otherwise not aligned.

The configuration of the channel 90 is similar to the configuration of the channel 52 described above. As shown in FIG. 3, the channel 90 includes a notch 96 defined in the rim 38 and the inner wall 40. The channel 90 also includes an opening 98 defined in the outer wall 44. The channel 90 is defined between a pair of opposing surfaces 100 that extend downwardly from the notch 96 and inwardly from the opening 98 to a pair of walls 102, 104. The channel 90 is further defined by another wall 106 that extends inwardly from the opening 98 to a lower end (not shown) of the wall 104. The walls 102, 104, 106 cooperate to define a stepped bottom wall of the channel 90 such that the channel 90 is divided into an upper segment 112 and a lower segment 114.

As shown in FIG. 3, the passageways 50 of the lower shell 30 also include a pair of channels 120, 122 defined in opposite sides 126, 128, respectively, of the lower shell 30. The channels 120, 122 define longitudinal axes 130, 132 and extend through the outer wall 44 and the inner wall 40 to the compartment 34. In the illustrative embodiment, the longitudinal axis 130 is coaxial with the longitudinal axis 132 such that the channels 120, 122 are aligned. It should be appreciated that in other embodiments the axes 130, 132 of the channels 120, 122 may be offset or otherwise not aligned. In the illustrative embodiment, the axes 130, 132 of the channels 120, 122 extend orthogonal to the axes 82, 94 of the channels 52, 90.

As shown in FIG. 3, the channel 120 includes a notch 136 defined in the rim 38 and the inner wall 40 on the side 126. The channel 120 also includes an opening 138 defined in the outer wall 44. The channel 120 is defined between a pair of opposing surfaces 140 that extend downwardly from the notch 136 and inwardly from the opening 138 to a pair of walls 142, 144. The channel 120 is further defined by another wall 146 that extends inwardly from the opening 138 to a lower end 148 of the wall 144.

As shown in FIG. 3, the walls 142, 144, 146 cooperate to define a stepped bottom wall of the channel 120 such that the channel 120 is divided into an upper segment 152 and a lower segment 154. Each opposing surface 140 includes a section 156 that extends downwardly from the notch 136 to the wall 142, which is positioned between the rim 38 and the lower end 46 of the outer wall 44. The sections 156 of the surfaces 140 and the wall 142 define the upper segment 152. Each opposing surface 140 also includes a section 158 that extends inwardly from the opening 138 to the wall 144, which extends downwardly from an edge 160 of the wall 142. The sections 158 of the surfaces 140, the wall 144, and the wall 146 define the lower segment 154 of the channel 120. It should be appreciated that in other embodiments the channel may have a substantially planar bottom wall. In other embodiments, the bottom wall of the channel 120 may be angled or sloped.

The configuration of the channel 122 is similar to the configuration of the channel 120 described above. As shown in FIG. 3, the channel 122 includes a notch 186 defined in the rim 38 and the inner wall 40 on the side 128 of the lower shell 30. The channel 122 also includes an opening 188 defined in the outer wall 44. The channel 122 is defined between a pair of opposing surfaces 190 that extend downwardly from the notch 186 and inwardly from the opening 188 to a pair of walls 192, 194. The channel 122 is further defined by another wall 196 that extends inwardly from the opening 188 to a lower end (not shown) of the wall 194. The walls 192, 194, 196 cooperate to define a stepped bottom wall of the channel 122 such that the channel 122 is divided into an upper segment 202 and a lower segment 204.

As described above, the passageways 50 defined in the lower shell 30 are the channels 52, 90, 120, 122 defined in the rim 38. It should be appreciated that in other embodiments the passageways 50 may be bores or through-holes that extend through the inner wall 40 and the outer wall 44 into the compartment 34. Additionally, in other embodiments additional or fewer passageways may be defined in the lower shell 30. For example, the shell may have only a single passageway defined therein.

As shown in FIG. 3, the compartment 34 of the lower shell 30 includes a number of positioning slots 206 that are sized and shaped to receive portions of the orthopaedic surgical instruments 12. As described above, the instruments 12 include a sensor module 16, and the slots 206 include a receiving slot 208 sized and shaped to receive the sensor module 16. The receiving slot 208 has an end 210 located on the side 54 of the lower shell 30 and another end 212 located on the opposite side 92 of the lower shell 30. In the illustrative embodiment, the channels 52, 90 open into the ends 210, 212, respectively, of the slot 208.

The end 210 of the receiving slot 208 is defined by a plurality of inner surfaces 214 of the inner wall 40, and the inner surface 214 are keyed to match the structure of the end 534 of the sensor module 16, as described in greater detail below. As shown in FIG. 3, the inner surfaces 214 include a substantially planar surface 216 located in an imaginary plane 218 positioned between the rim 38 and the base wall 42 of the lower shell 30. The inner surfaces 214 also include another substantially planar surface 220 located in an imaginary plane 222 positioned between the plane 218 and the rim 38. An oblique surface 224 connects the surfaces 216, 220. A groove 226 extends through the surfaces 216, 220, 224 to the base wall 42. The inner surfaces 214 also include a pair of surfaces 228 extending upwardly from the surfaces 216, 220, 224.

The opposite end 212 of the receiving slot 208 is defined by a plurality of inner surfaces 230 of the inner wall 40 that are keyed to match the structure of the tibial paddle 504 of the sensor module 16, as described in greater detail below. As shown in FIG. 3, the inner surfaces 230 include a substantially planar surface 232 located in an imaginary plane 234 positioned between the rim 38 and the base wall 42 of the lower shell 30. The inner surfaces 230 also include a curved surface 236 that extends vertically from the surface 232.

As described in reference to FIG. 18 below, the surgical instruments 12 may include another sensor module 600, and the positioning slots 206 of the lower shell 30 include another receiving slot 240 sized and shaped to receive the sensor module 600. The receiving slot 240 includes the same end 210 as the receiving slot 208, which is located on the side 54 of the lower shell 30. The receiving slot 240 has another end 242 located on the opposite side 92 of the lower shell 30. The end 242 of the receiving slot 240 is defined by a plurality of inner surfaces 244 of the inner wall 40 that are keyed to match the structure of the larger tibial paddle 602 of the sensor module 600 (see FIG. 18), as described in greater detail below. As shown in FIG. 3, the inner surfaces 244 include a substantially planar surface 246 located in the imaginary plane 234. The inner surfaces 244 also include a curved surface 248 that extends vertically from the surface 246. A groove 238 extends through the planar surface 246 to the base wall 42.

As described above, the surgical instruments 12 also include an adaptor 18 for the sensor module 16, and the positioning slots 206 of the lower shell 30 also include a pocket 250 sized to receive the upper retainer clips 556 of the adaptor 18. In the illustrative embodiment, the pocket 250 is positioned adjacent to the end 210 of the receiving slots 208, 240. The pocket 250 includes an opening 252 defined in a surface 254 of the inner wall 40, and a cylindrical inner surface 256 extends downwardly from the opening 252 to a planar surface 258. Another opening 260 is defined in the planar surface 258, and another inner surface 262 extends downwardly from the opening 260. The surfaces 256, 258, 262 cooperate to define a cavity 264 of the pocket 250. The pocket 250 also includes a channel 266 that extends downwardly from the surface 254 of the inner wall 40. The channel 266 is sized to receive an anti-rotation key 560 of the adaptor 18.

As described above, the surgical instruments 12 also include the display module 20 for the sensor module 16. The positioning slots 206 of the lower shell 30 also include a receiving slot 270 sized and shaped to receive the lower side 598 of the hand-held display module 20. As shown in FIG. 3, the receiving slot 270 is defined by a pair of ribs 272, 274 extending upwardly from the base wall 42. The base wall 42 has a substantially planar surface 276 that extends between the ribs 272, 274. The ribs 272, 274 and the surface 276 are keyed to match the structure of the lower side 598 of the display module 20, and, in the illustrative embodiment, the rib 274 includes a slot 280 sized to receive a rib 588 formed on the lower side 598 of the display module 20, as described in greater detail below.

Figure 4:
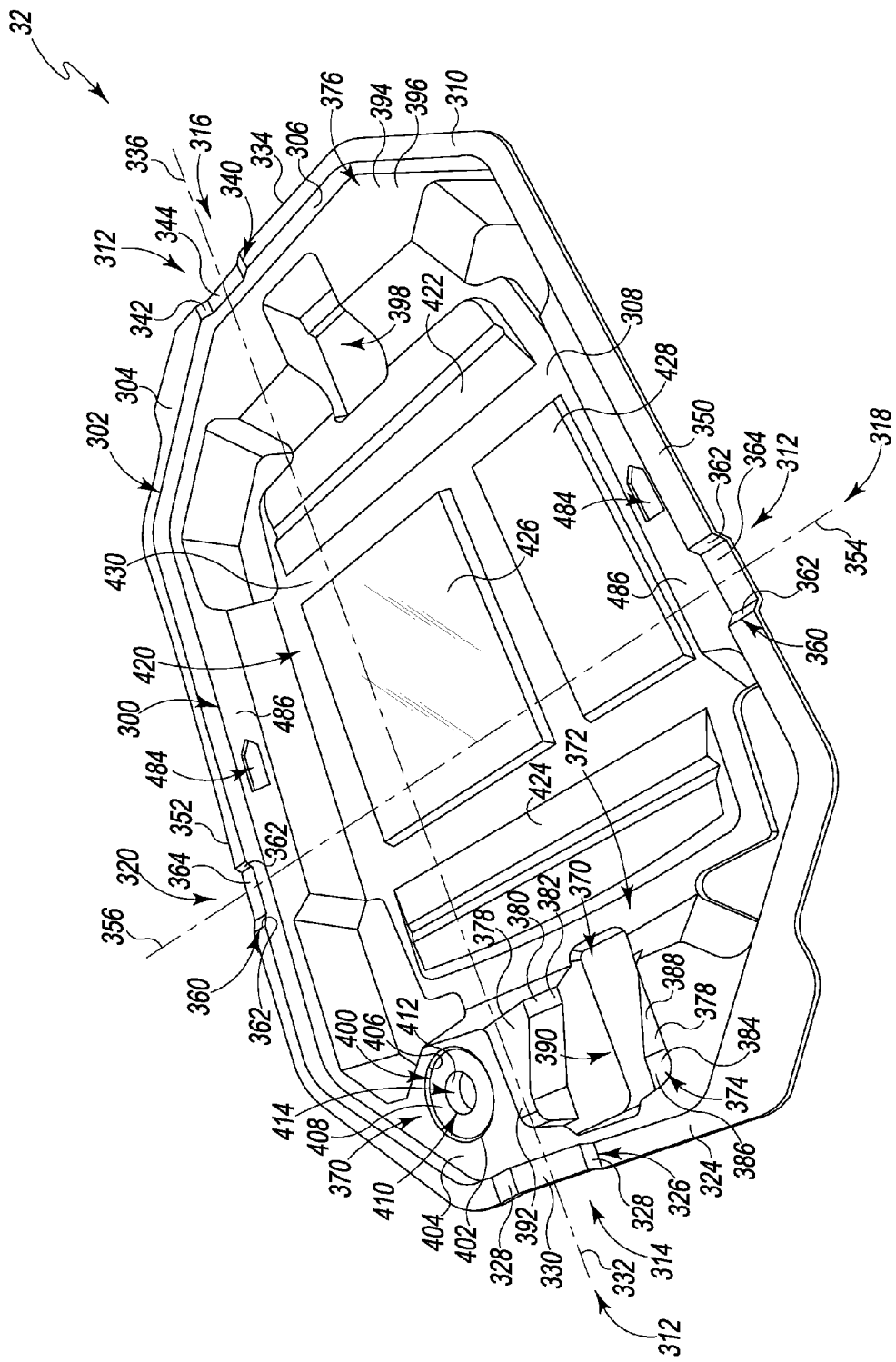
FIG. 4 is a perspective view of an upper shell of the surgical instrument container of FIG. 2.

As described above, the instrument container 14 of the system 10 also includes an upper shell 32 configured to be coupled to the lower shell 30. Referring now to FIG. 4, the upper shell 32 of the container 14 defines a compartment 300 having an opening 302 that is defined by a rim 304. The upper shell 32 includes an inner wall 306 that extends inwardly from the opening 302 to a base wall 308. The walls 306, 308 cooperate to define the compartment 300. The upper shell 32 also includes a flange 310 that extends outwardly from the rim 304. As described in greater detail below, a number of passageways 312 are defined in the upper shell 32, and each passageway 312 is sized to permit fluid, such as, for example, an instrument sterilization gas, to advance into and out of the compartment 300.

The passageways 312 of the upper shell 32 include channels 314, 316, 318, 320, which correspond to the channels 52, 90, 120, 122 of the lower shell 30. As shown in FIG. 4, the channel 314 is defined in a side 324 of the upper shell 32. The channel 314 includes a notch 326 defined in the rim 304. A pair of opposing sloped surfaces 328 extends downwardly from the notch 326 to a substantially planar surface 330. The surfaces 328, 330 cooperate to define the channel 314.

The channel 314 of the upper shell 32 defines a longitudinal axis 332 and extends through the inner wall 306 and the flange 310 to the compartment 300. The channel 316 of the passageways 312 is defined in the side 334 of the upper shell 32 opposite the side 324. The channel 316 also defines a longitudinal axis 336 and extends through the inner wall 306 and the flange 310 to the compartment 300. In the illustrative embodiment, the longitudinal axis 332 is coaxial with the longitudinal axis 336 such that the channels 314, 316 are aligned. It should be appreciated that in other embodiments the axes 332, 336 of the channels 314, 316 may be offset or otherwise not aligned.

The configuration of the channel 316 is similar to the configuration of the channel 314 described above. The channel 316 includes a notch 340 defined in the rim 304. A pair of opposing sloped surfaces 342 extends downwardly from the notch 340 to a substantially planar surface 344. The surfaces 342, 344 cooperate to define the channel 316.

As shown in FIG. 4, the passageways 312 of the upper shell 32 also include a pair of channels 318, 320 defined in opposite sides 350, 352, respectively, of the upper shell 32. The channels 318, 320 define longitudinal axes 354, 356, respectively, and extend through the inner wall 306 and the flange 310 to the compartment 300. In the illustrative embodiment, the longitudinal axis 354 is coaxial with the longitudinal axis 356 such that the channels 318, 320 are aligned. It should be appreciated that in other embodiments the axes 354, 356 of the channels 318, 320 may be offset or otherwise not aligned. Additionally, as shown in FIG. 4, the axes 354, 356 of the channels 318, 320 extend orthogonal to the axes 332, 336 of the channels 314, 316.

The configurations of the channels 318, 320 are similar to the configurations of the channels 314, 316 described above. Each of the channels 318, 320 includes a notch 360 defined in the rim 304. A pair of opposing sloped surfaces 362 extends downwardly from the notch 360 to a substantially planar surface 364. The surfaces 362, 364 cooperate to define the channel 318 and the channel 320.

As described above, the passageways 312 defined in the upper shell 32 are the channels 314, 316, 318, 320 defined in the rim 304. It should be appreciated that in other embodiments the passageways 312 may be bores or through-holes that extend through the upper shell 32. For example, in other embodiments, the flange 310 may be omitted and the passageways 312 may extend through the inner wall 306 and the outer wall 366 of the upper shell 32 to the compartment 34. Additionally, in other embodiments additional or fewer passageways may be defined in the upper shell 32. For example, the shell may have only a single passageway defined therein.

As shown in FIG. 4, the compartment 300 of the upper shell 32 includes a number of positioning slots 370 that are sized and shaped to receive portions of the orthopaedic surgical instruments 12. As described above, the instruments 12 include a sensor module 16, and the slots 370 include a receiving slot 372 sized and shaped to receive the sensor module 16. The receiving slot 372 has an end 374 located on the side 324 of the upper shell 32 and another end 376 located on the opposite side 334 of the upper shell 32.

The end 374 of the receiving slot 372 is defined by a plurality of inner surfaces 378 of the inner wall 306 that are keyed to match the structure of the end 534 of the sensor module 16, as described in greater detail below. As shown in FIG. 4, the inner surfaces 378 include a substantially planar surface 380 located in an imaginary plane 382 positioned between the rim 304 and the base wall 308 of the upper shell 32. The inner surfaces 378 also include another substantially planar surface 384 located in an imaginary plane 386 positioned between the plane 382 and the rim 304. An oblique surface 388 connects the surfaces 380, 384. A groove 390 extends through the surfaces 380, 384, 388 to the base wall 42. The inner surfaces 378 defining the slot 372 also include a pair of surfaces 392 extending upwardly from the surfaces 380, 384, 388.

The opposite end 376 of the receiving slot 372 includes a substantially planar surface 394 located in an imaginary plane 396 positioned between the rim 304 and the base wall 308 of the upper shell 32. The surface 394 is configured to engage the tibial paddle 504 of the sensor module 16. A groove 398 extends through the planar surface 394 to the base wall 308.

As described above, the surgical instruments 12 also include an adaptor 18 for the sensor module 16. As shown in FIG. 4, the positioning slots 370 of the upper shell 32 also include a pocket 400 sized to receive the lower retainer clips 558 of the adaptor 18. In the illustrative embodiment, the pocket 400 is positioned adjacent to the end 374 of the receiving slot 372. The pocket 400 includes an opening 402 defined in a surface 404 of the inner wall 306, and a cylindrical inner surface 406 extends downwardly from the opening 402 to a planar surface 408. Another opening 410 is defined in the planar surface 408, and another inner surface 412 extends downwardly from the opening 410. The surfaces 406, 408, 412 cooperate to define a cavity 414 of the pocket 400.

As described above, the surgical instruments 12 also include the display module 20 for the sensor module 16. The positioning slots 370 of the upper shell 32 also include a receiving slot 420 sized and shaped to receive the upper side 576 of the hand-held display module 20. As shown in FIG. 4, the receiving slot 420 is defined by a pair of ribs 422, 424 positioned on each side of a pair of protrusions 426, 428. The base wall 308 of the upper shell 32 has a substantially planar surface 430 that extends between the ribs 422, 424 and the protrusions 426, 428. The ribs 422, 424, the protrusions 426, 428, and the surface 430 are keyed to match the structure of the upper side 576 of the display module 20, as described in greater detail below.

Referring now to FIGS. 5-8, the upper shell 32 is configured to be secured to the lower shell 30 in a number of different orientations to form the container 14. In each orientation, the rim 38 of the lower shell 30 extends through the opening 302 of the upper shell 32, and the outer wall 44 of the lower shell 30 engages the inner wall 306 of the upper shell 32. The compartments 34, 300 of the shells 30, 32 cooperate to define a chamber 450 within the container 14. In the illustrative embodiment, the orientations include an open orientation in which fluid is permitted to advance into and out of the chamber 450. The orientations also include a closed orientation in which fluid is prevented advancing into and out of the chamber 450.

Figure 5:
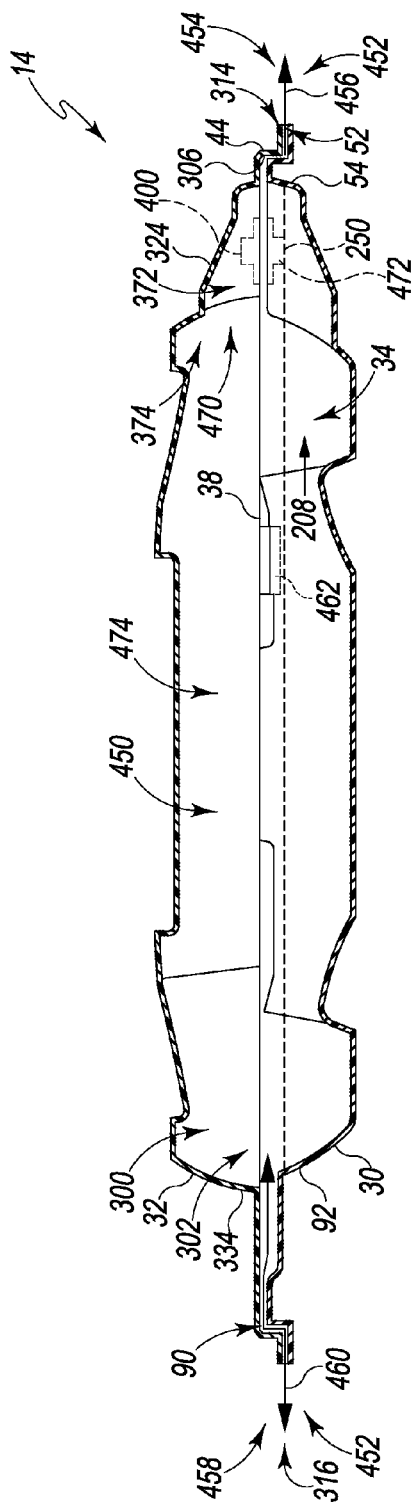
FIG. 5 is a cross-sectional side elevation view of the surgical instrument container of FIG. 2 showing the lower shell and the upper shell secured together in one orientation.
Figure 7:
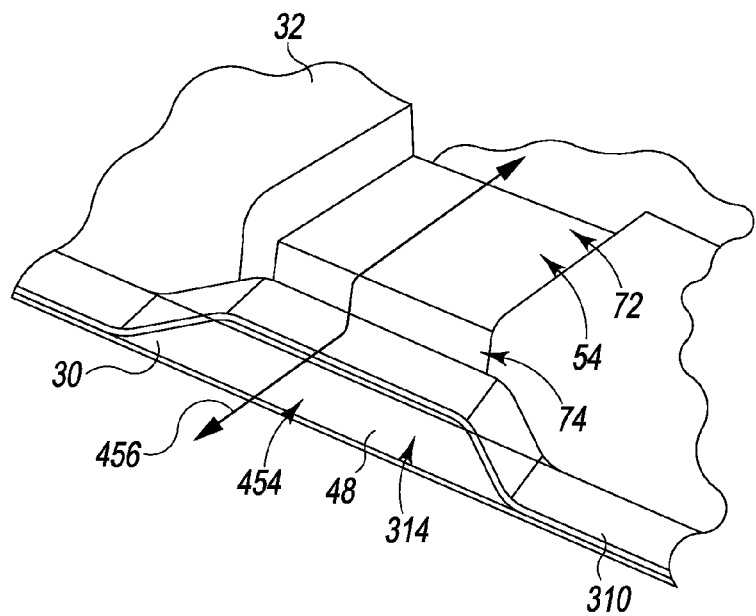
FIG. 7 is a perspective view of a vent formed in the container when the instrument container is assembled as shown in FIG. 5.
Figure 8:
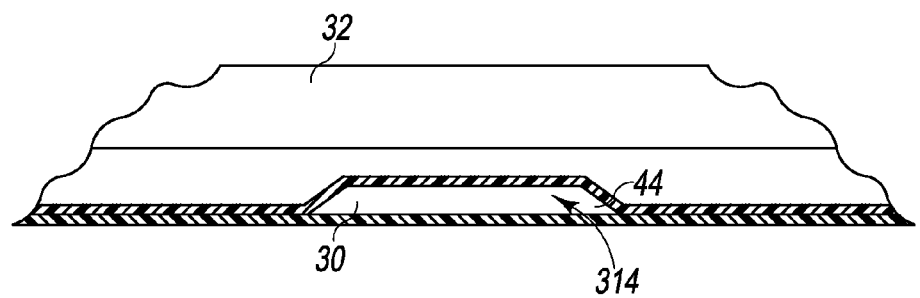
FIG. 8 is a perspective view of a passageway of the lower shell when the instrument container is assembled as shown in FIG. 6.

As shown in FIG. 5, the upper shell 32 may be secured to the lower shell 30 in the open orientation such that the passageways 50 of the lower shell 30 are aligned with the passageways 312 of the upper shell 32. In the open orientation, the passageways 50, 312 define a plurality of vents 452 that permit fluid to advance into and out of the chamber 450. For example, as shown in FIGS. 5 and 7, the channel 52 of the lower shell 30 is aligned with the channel 314 of the upper shell 32 to define a vent 454 extending through the sides 54, 324 of the shells 30, 32 to the chamber 450. Fluid is permitted to advance through the vent 454 in the directions indicated by arrow 456 such that the fluid may advance into and out of the chamber 450.

Similarly, as shown in FIG. 5, the channel 90 of the lower shell 30 is aligned with the channel 316 of the upper shell 32 to define a vent 458 extending through the side 92, 334 of the shells 30, 32. Fluid is permitted to advance through the vent 458 in the directions indicated by arrow 460. The channels 120, 320 of the shells 30, 32, respectively, and the channels 122, 318 of the shells 30, 32, respectively, are similarly aligned to define additional vents 464, 462 (see FIG. 14) through the container 14.

When the shells 30, 32 are coupled together in the open orientation, the receiving slots 208, 372 of the shells 30, 32, respectively, define a receptacle 470 sized to receive the sensor module 16. As shown in FIG. 5, the end 210 of the receiving slot 208 and the end 374 of the receiving slot 372 are aligned such that the end 534 of the sensor module 16 may be positioned therein. Additionally, the pockets 250, 400 of the shells 30, 32, respectively, are aligned to define a receptacle 472 sized to receive the adaptor 18.

Figure 6:
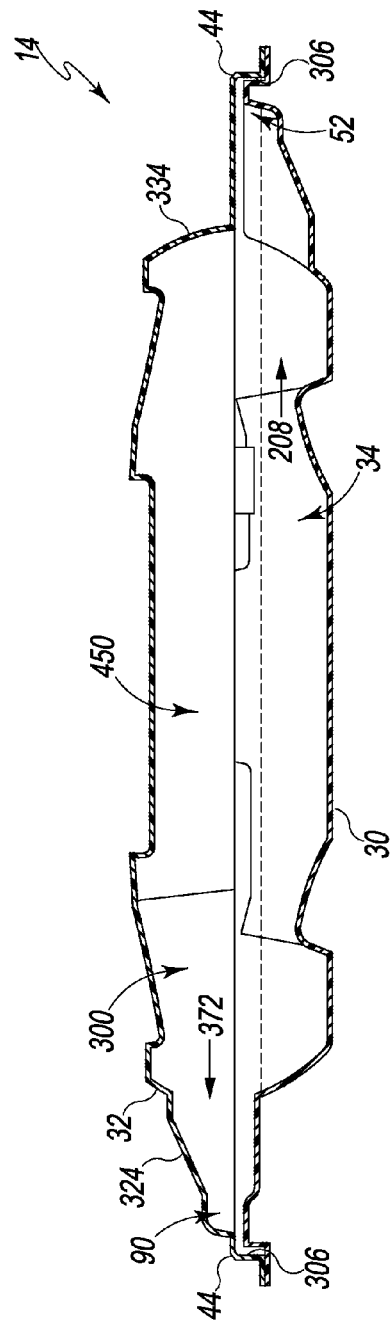
FIG. 6 is a cross-sectional side elevation view similar to FIG. 4 of the surgical instrument container showing the lower shell and the upper shell secured together in another orientation.

As shown in FIG. 6, the upper shell 32 may be secured to the lower shell 30 in the closed orientation such that the inner wall 306 of the upper shell 32 is positioned over the passageways 50 of the lower shell 30 such that no vents are defined in the container 14 and fluid is not permitted to advance into and out of the chamber 450. In that way, a shown in FIG. 8, the passageways 312 of the upper shell 32 face the outer wall 44 of the lower shell 30, and the passageways 50, 312 are spaced apart from each other. Additionally, when the shells 30, 32 are coupled together in the closed orientation, the receiving slots 270, 420 of the shells 30, 32, respectively, define a receptacle 474 sized to receive the display module 20.

Figure 9:
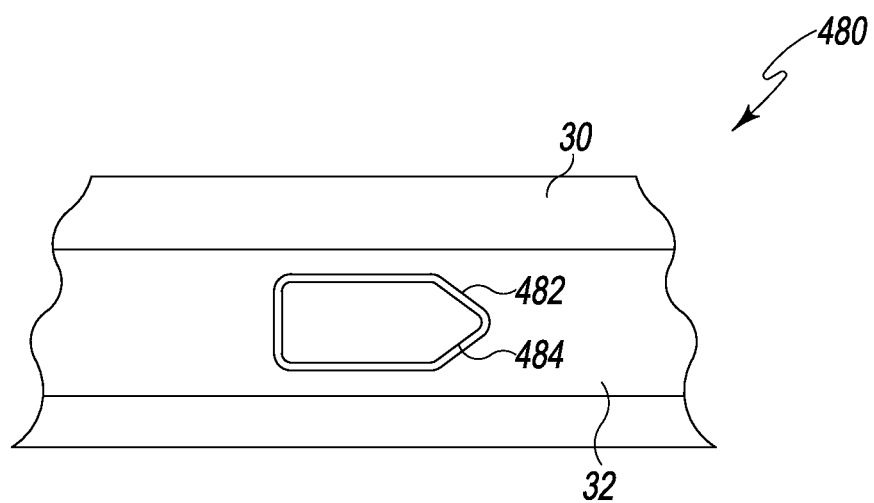
FIG. 9 is a top plan view of an indicator of the instrument container when the instrument container is assembled as shown in FIG. 5.
Figure 10:
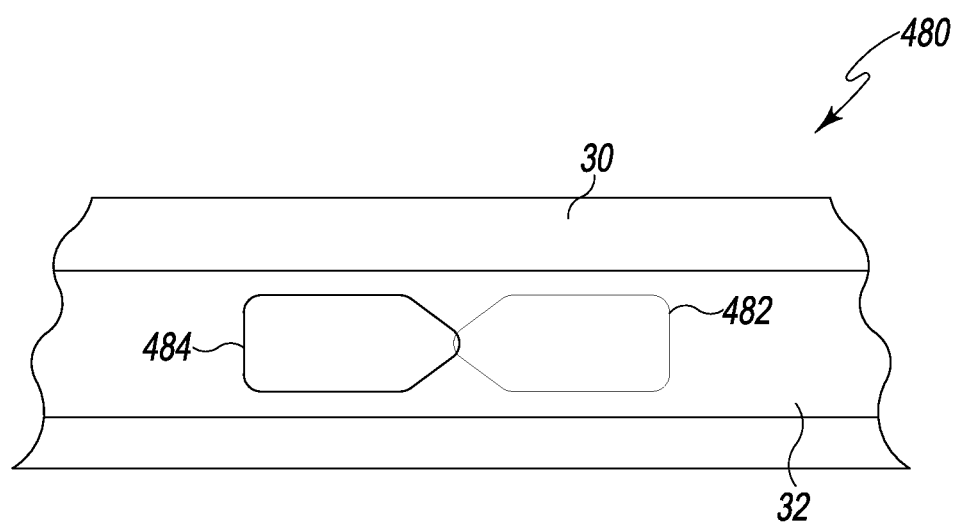
FIG. 10 is a top plan view of the indicator of the instrument container when the instrument container is assembled as shown in FIG. 6.

As shown in FIGS. 9 and 10, the container 14 includes an orientation indicator 480 that provides an indication to the user of the orientation of the upper shell 32 relative to the lower shell 30. As shown in FIG. 3, the indicator 480 includes a pair of arrows 482 that are defined in the rim 38 on each side 126, 128 of the lower shell 30. As shown in FIG. 4, the indicator 480 also includes a pair of arrows 484 that is defined in a surface 486 of the inner wall 306 of the upper shell 32. In other embodiments, the arrows 482, 484 may be etched, imprinted, or other applied to the shells 30, 32. It should also be appreciated that in other embodiments the indicator 480 may take the form of other graphics, text, or other media.

In the illustrative embodiment, the arrows 482, 484 point in the same direction when the upper shell 32 is coupled to the lower shell 30 in the open orientation. As shown in FIG. 9, one of the arrows 484 of the upper shell 32 is positioned over the one of the arrows 482 of the lower shell 30 to indicate the vents 452 are formed in the container 14. As a result, the user is informed that fluid is permitted to advance into and out of the chamber 450.

When the upper shell 32 is coupled to the lower shell 30 in the closed orientation, the arrows 482, 484 point in opposing directions. As shown in FIG. 10, the arrows 484 of the upper shell 32 point toward the arrows 482 of the lower shell 30 while the arrows 482 point toward the arrows 484. As a result, the user is informed that fluid is prevented from advancing into and out of the chamber 450.

As described above, the system 10 also includes a sensor module 16, an adaptor 18, and a display module 20. In the illustrative embodiment, the sensor module 16 of the system 10 is configured to be inserted into a patient's joint and provide a visual indication of the joint forces to an orthopaedic surgeon. The sensor module 16 may also be configured to transmit joint force data to the hand-held display module 20. In response, the display module 20 is configured to display the joint force data, or data derived therefrom, to an orthopaedic surgeon.

Figure 11:
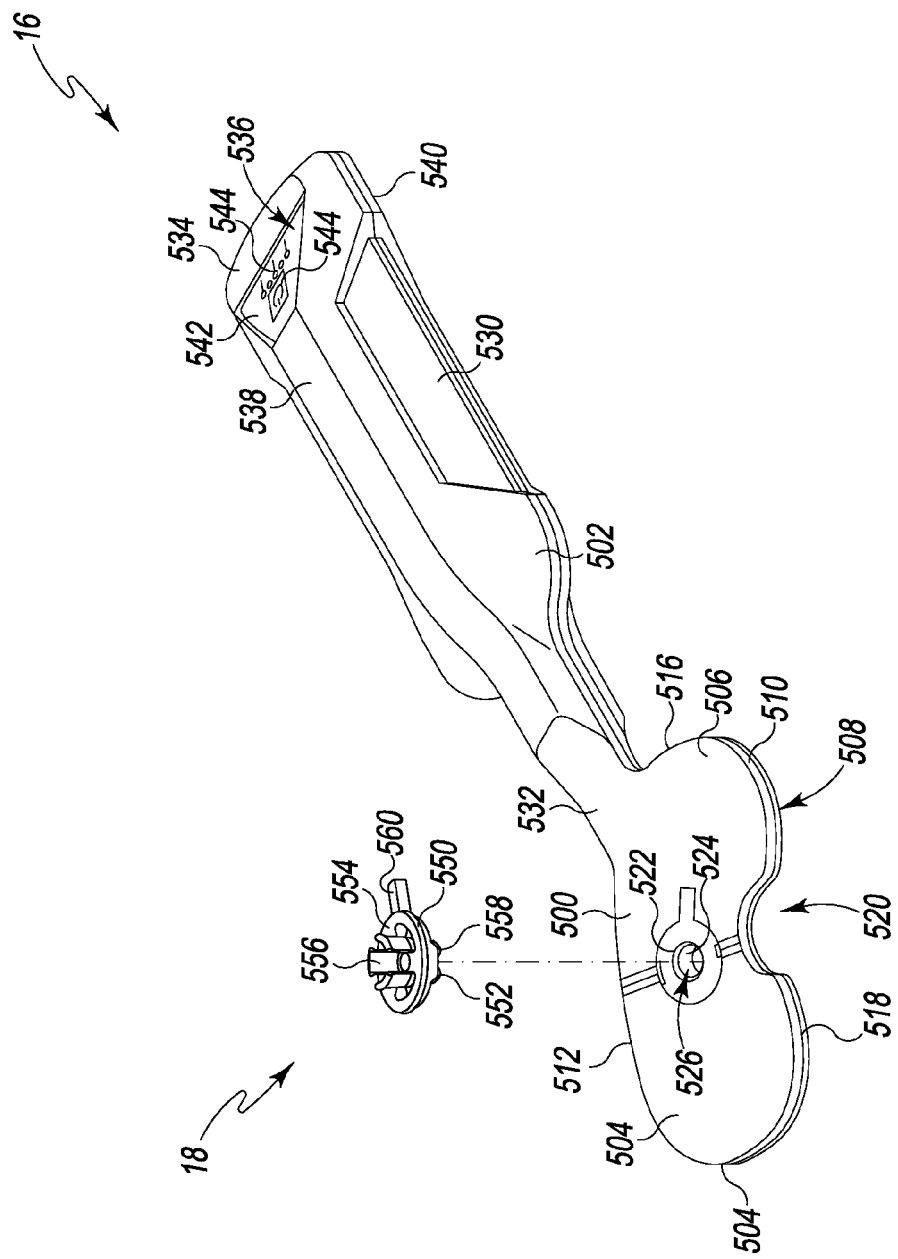
FIG. 11 is an exploded perspective view of an orthopaedic surgical instrument of the system of FIG. 1.

Referring now to FIG. 11, the sensor module 16 includes a sensor housing 500 and a handle 502 coupled to the sensor housing 500. The sensor housing 500 is sized and shaped to be positioned in a joint of the patient. In the illustrative embodiment, the sensor housing 500 is a tibial paddle 504, which is shaped to be positioned in a knee joint of the patient. It should be appreciated that in other embodiments the sensor housing 500 may be configured to be used with other joints of the patient.

The tibial paddle 504 includes an upper surface 506, a lower surface 508, and a curved side wall 510 that extends between the surfaces 506, 508. The side wall 510 includes a curved anterior side 512, a curved lateral side 514, a curved medial side 516, and a curved posterior side 518. Each side is shaped to approximate the shape a tibial bearing of an orthopaedic knee prosthesis. It should be appreciated that the "upper surface" and the "lower surface" may be reversed depending on the operative side of the patient. Similarly, the "medial side" and the "lateral side" may be reversed depending on whether the surgeon uses a medial approach or lateral approach during surgery. The posterior side 518 includes a posterior notch 520 to allow the tibial paddle 504 to be positioned around the soft tissue of the patient's joint such as the posterior cruciate ligament. The overall size of the tibial paddle 504 may be selected based on the particular anatomical structure of the patient. For example, in some embodiments, the tibial paddle 504 may be provided in various sizes to accommodate patients of varying sizes.

The tibial paddle 504 also includes an opening 522 defined in the upper surface 506. An inner wall 524 extends downwardly from the opening 522 to define a vertical aperture 526 in the paddle 504. The aperture 526 is sized to receive the lower retainer clips 558 of the adaptor 18.

As shown in FIG. 11, the handle 502 includes a body 530 having an end 532 coupled to the tibial paddle 504. The opposite end 534 of the body 530 includes a pair of displays 536, which are positioned on opposite sides 538, 540 of the body 530. Each display 536 includes an angled control surface 542 including a number of controls 544. The controls 544 may include, for example, buttons and indicator lights for the sensor module 16. In other embodiments, the displays 536 may be embodied as other types of displays such as liquid crystal displays, segmented displays, and/or the like.

As described above, the surgical instruments 12 include an adaptor 18 that is configured to be secured to the tibial paddle 504. As shown in FIG. 11, the adaptor 18 includes a hub 550 having a bottom side 552, which contacts or otherwise confronts the tibial paddle 504 when the adaptor 18 is coupled thereto, and a top side 554 opposite the bottom side 552. Illustratively, the hub 550 has a circular shape, or near-circular shape. A set of upper retainer clips 556 extend upwardly from the top side 554, a set of lower retainer clips 558 extend downwardly from the bottom side 552, and an anti-rotation key 560 that extends outwardly from the hub 550. In the illustrative embodiment, the upper retainer clips 556 are larger than the lower retainer clips 558 such that the upper retainer clips 556 cannot be inserted into the vertical aperture 526 of the tibial paddle 504.

Figure 12:
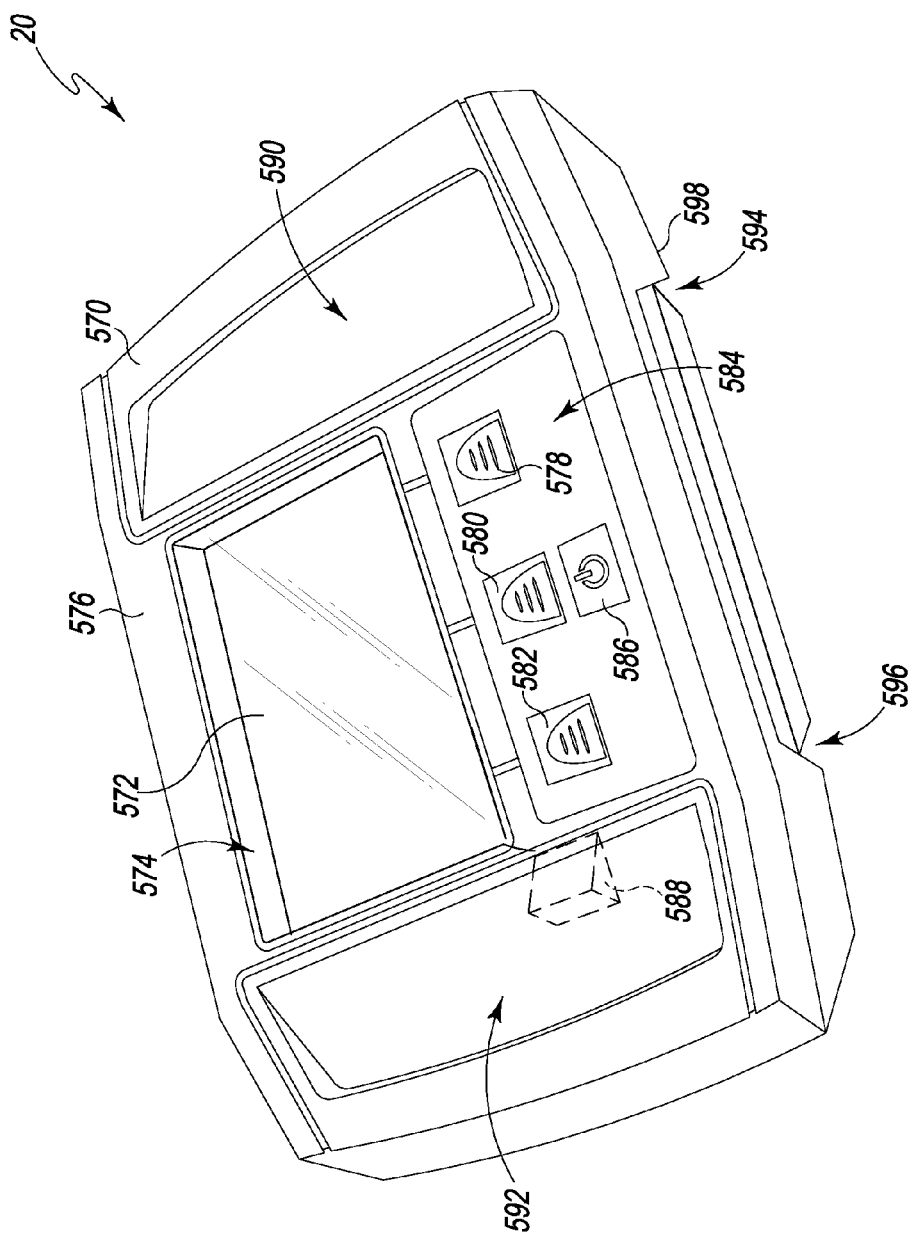
FIG. 12 is a perspective view of another orthopaedic surgical instrument of the system of FIG. 1.

Referring now FIG. 12, the hand-held display module 20 includes a housing 570. The display module 20 also includes a display 572 positioned in a slot 574 defined in an upper side 576 of the housing 570. A plurality of user input buttons 578, 580, 582 are positioned in another slot 584 defined in the upper side 576 of the housing 570 below the display 572. The display module 20 also includes a power button 586 positioned in the slot 584. The slots 574, 584 are positioned between a pair of grooves 590, 592 defined in the upper side 576 of the housing 570. The housing 570 of the display module 20 also includes a pair of grooves 594, 596 defined in the lower side 598 thereof. A rib 588 is formed on the lower side 598 and extends transverse to the groove 596.

Figure 13:
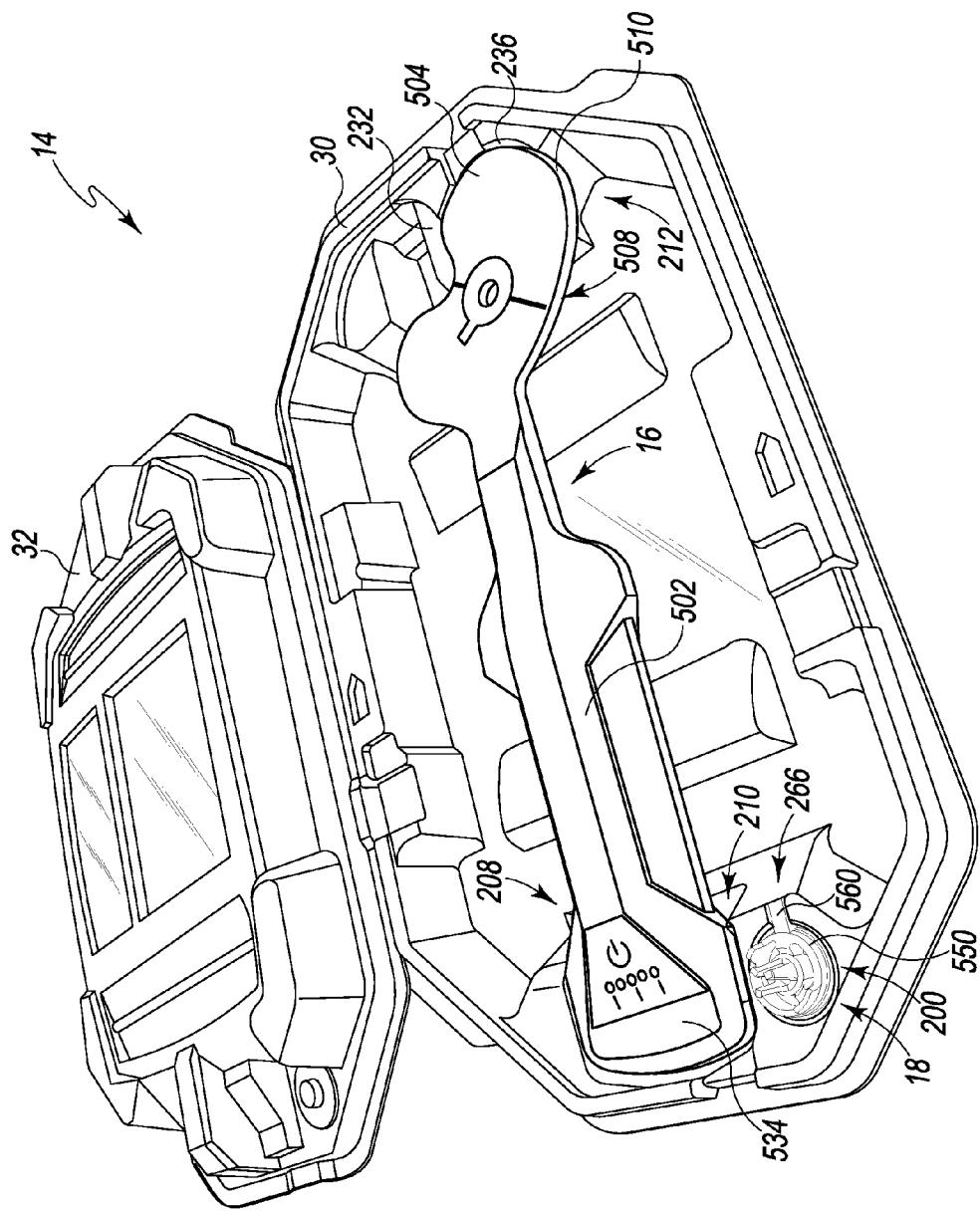
FIG. 13 is a perspective view of the disassembled surgical instrument container with the orthopaedic surgical instrument of FIG. 11 positioned in the lower shell.
Figure 14:
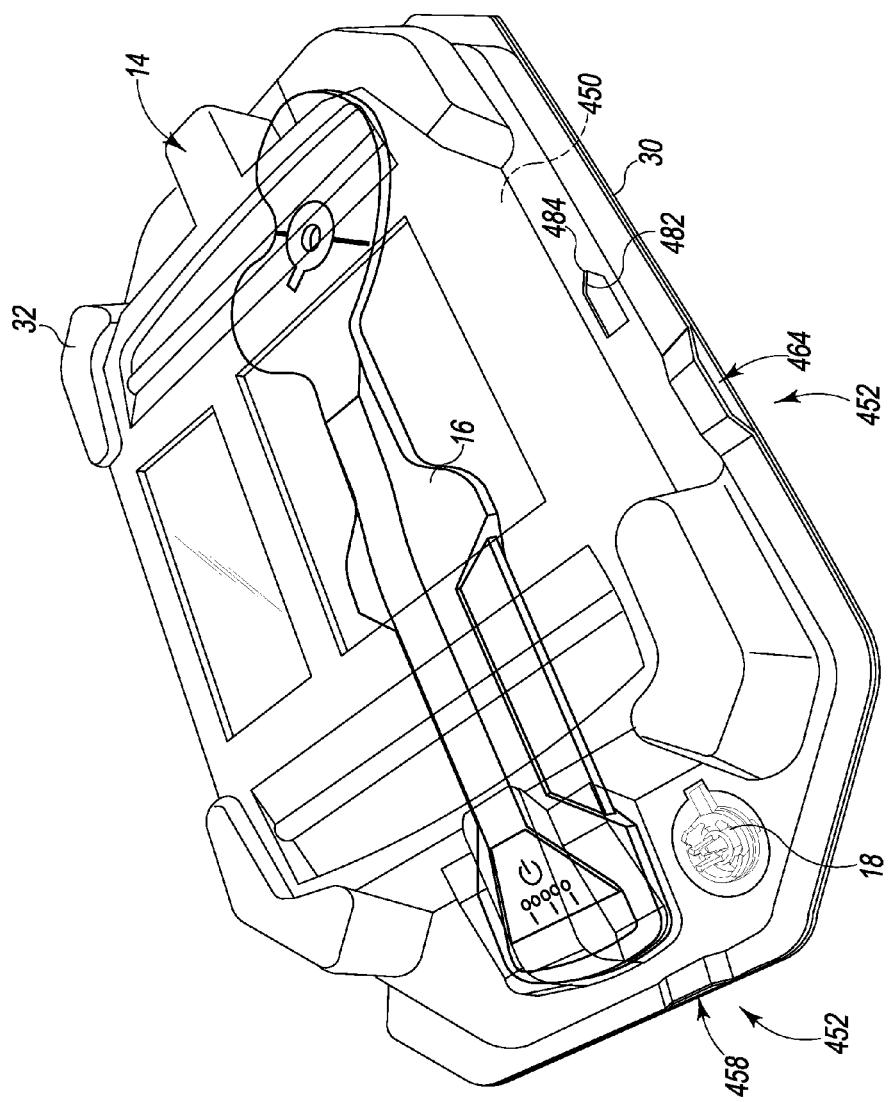
FIG. 14 is a perspective view of the assembled surgical instrument container showing the orthopaedic surgical instrument of FIG. 11 positioned therein.
Figure 15:
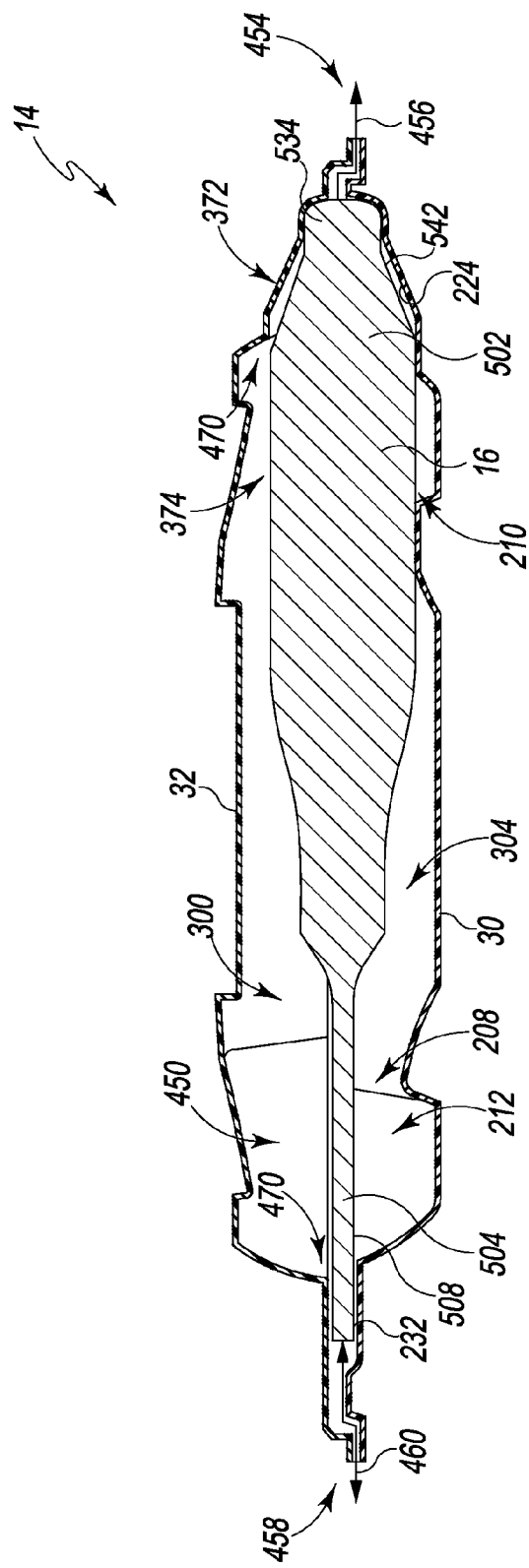
FIG. 15 is a cross-sectional side elevation view of the surgical instrument container assembled as shown in FIG. 14.

In use, the container 14 is capable of carrying any of the surgical instruments 12 depending on the orientation of the upper shell 32 relative to the lower shell 30. Referring now to FIGS. 13-15, the upper shell 32 is positioned in the open orientation relative to the lower shell 30, and the sensor module 16 is received in the lower shell 30. When received in the lower shell 30, the end 534 of the sensor handle 502 is positioned in the end 210 of the receiving slot 208 while the tibial paddle 504 is positioned in the end 212 of the receiving slot 208. As described above, the end 210 of the receiving slot 208 is keyed to match the structure of the end 534 of the sensor handle 502. For example, as shown in FIG. 15, the angled control surface 542 of the display 536 on the sensor handle 502 is engaged with the oblique surface 224 that defines the receiving slot 208. Similarly, at the other end 212 of the slot 208, the planar surface 232 of the lower shell 30 engages the lower surface 508 of the tibial paddle 504, and the curved surface 236 engages the curved side wall 510 of the paddle 504.

As shown in FIG. 13, the adaptor 18 is received in the pocket 200. Specifically, the top side 554 of the hub 550 is engages the surface 258 and the upper retaining clips 556 are received in the cavity 264. The anti-rotation key 560 of the adaptor 18 is positioned in the channel 266 defined in the shell 30.

When the sensor module 16 is properly positioned in the lower shell 30, the upper shell 32 may be lowered onto the lower shell 30 in the open orientation. As described above, the rim 38 of the lower shell 30 extends through the opening 302 of the upper shell 32, and the outer wall 44 of the lower shell 30 engages the inner wall 306 of the upper shell 32. The compartments 34, 300 of the shells 30, 32 cooperate to define a chamber 450 within the container 14. As shown in FIG. 14, a plurality of vents 452 are defined in the container 14 in the open orientation, which permit fluid to advance into and out of the chamber 450. The indicator arrows 484 of the upper shell 32 are positioned over the arrows 482 of the lower shell 30 to indicate the vents 452 are formed in the container 14. As a result, the user is informed that fluid is permitted to advance into and out of the chamber 450.

As shown in FIG. 15, the receiving slots 208, 372 of the shells 30, 32, respectively, define a receptacle 470 that receives the sensor module 16. The end 210 of the receiving slot 208 and the end 374 of the receiving slot 372 are aligned such that the end 534 of the sensor module 16 may be positioned therein. The grooves 226, 390 defined in the surfaces 214, 378 of the receiving slots 208, 372 are aligned with controls 544 of the sensor module 16 to prevent accidental activation of the sensor module 16 when it is positioned in the container 14. Additionally, the other ends 212, 376 of the slots 208, 372 are aligned to receive the tibial paddle 504 of the sensor module 16. Similarly, the pockets 250, 400 of the shells 30, 32, respectively, are aligned to define a receptacle 472 that receives the adaptor 18. In that way, the sensor module 16 and the adaptor 18 may be carried together in the container 14.

Figure 16:
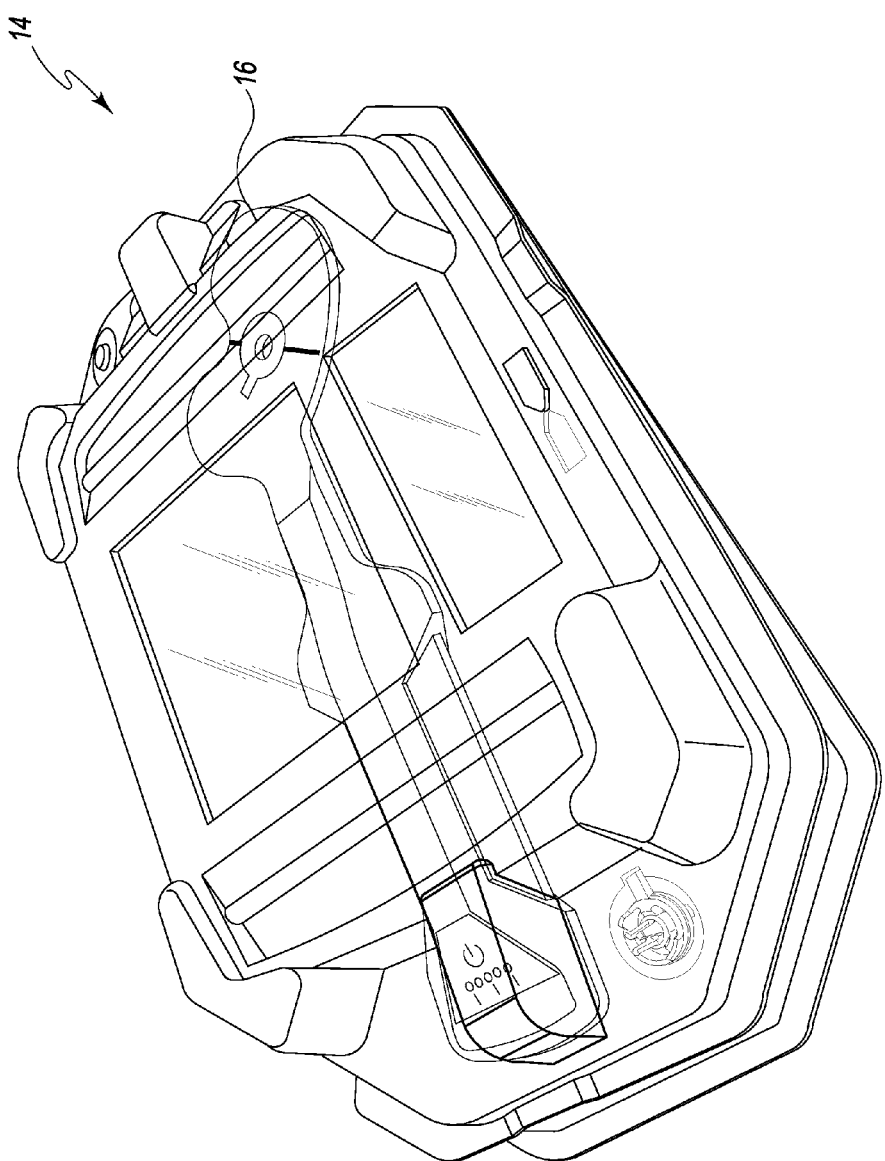
FIG. 16 is another perspective view of the instrument container showing the orthopaedic surgical instrument of FIG. 11 positioned therein.
Figure 17:
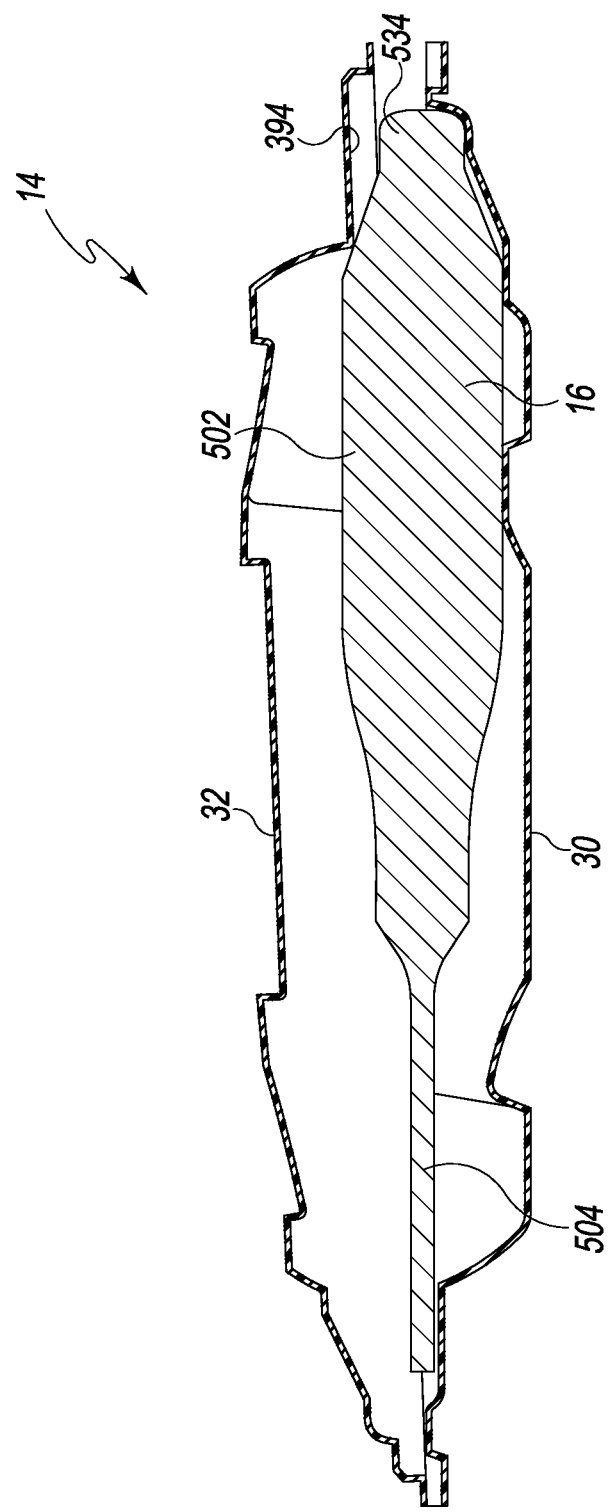
FIG. 17 is a cross-sectional side elevation view of the surgical instrument container when assembled as shown in FIG. 16.

As shown in FIGS. 16 and 17, the interaction between the sensor module 16 prevents the upper shell 32 from being attached to the lower shell 30 in the closed orientation when the sensor module 16 is positioned in the lower shell 30. In the illustrative embodiment, the end 534 of the sensor handle 502 is configured to engage the planar surface 394 of the upper shell 32 such that the upper shell 32 cannot be secured to the lower shell 30. In that way, the upper shell 32 can be attached to the lower shell 30 in only the open orientation when the sensor module 16 is received in the lower shell 30.

Figure 18:
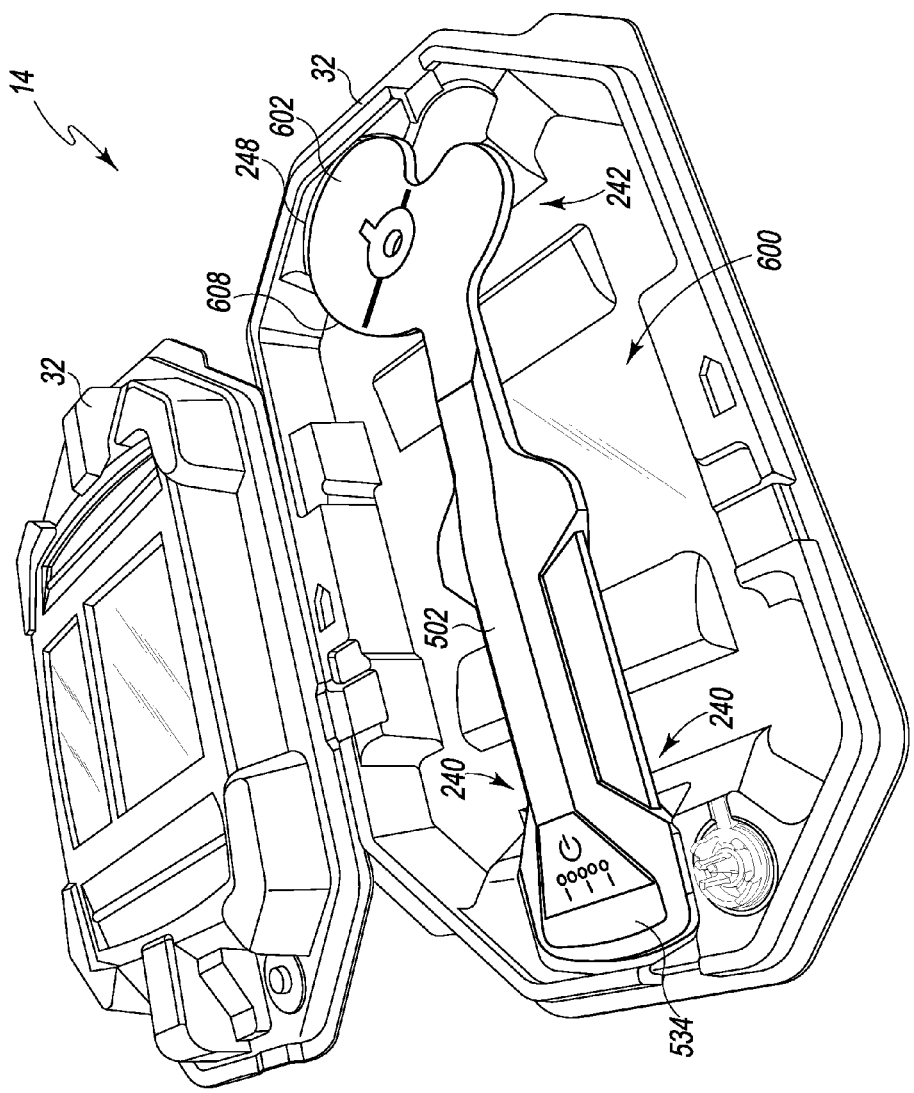
FIG. 18 is another perspective view of the surgical instrument container with another orthopaedic surgical instrument positioned in the lower shell.

Referring now FIG. 18, the upper shell 32 is oriented in the open orientation relative to the lower shell 30, and another, larger sensor module 600 is received in the lower shell 30. The sensor module 600, like the sensor module 16, includes a sensor handle 502. When received the sensor module 600 is received in the lower shell 30, the end 534 of the sensor handle 502 is positioned in the end 210 of the receiving slot 240. As described above, the end 210 of the receiving slot 240 is keyed to match the structure of the end 534 of the sensor handle 502.

As shown in FIG. 18, the sensor module 600 also includes a tibial paddle 602, which is secured to the handle 502. The tibial paddle 602 includes an upper surface 604, a lower surface 606, and a curved side wall 608. In the illustrative embodiment, the tibial paddle 602 is larger than the tibial paddle 504 of the sensor module 16. The tibial paddle 602 is positioned in the end 242 of the receiving slot 240. The planar surface 244 of the lower shell 30 engages the lower surface 606 of the tibial paddle 602, and the curved surface 248 engages the curved side wall 608 of the paddle 602. When the upper shell 32 is in the open orientation, the upper shell 32 may be attached to the lower shell 30 as described above when the sensor module 600 is received therein.

Figure 19:
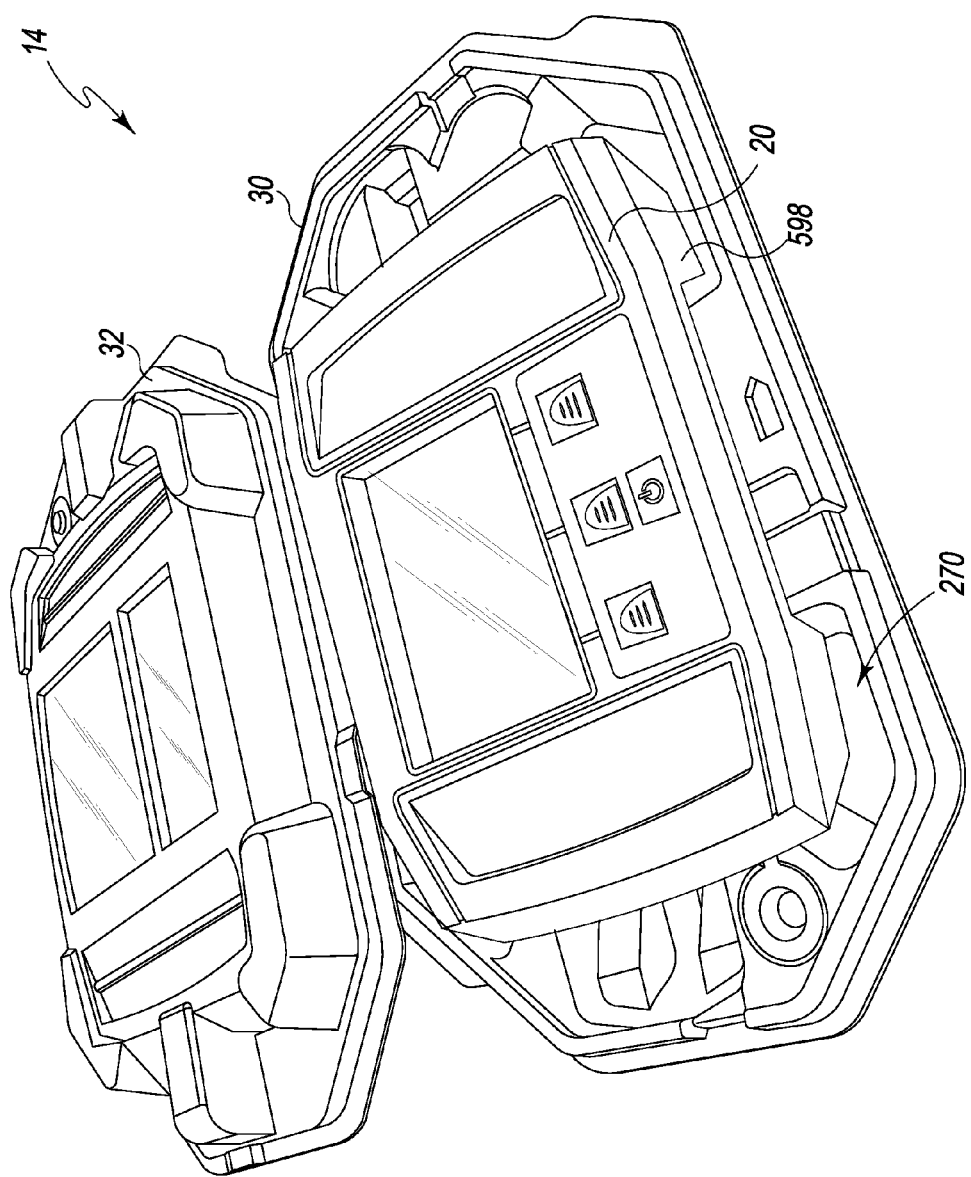
FIG. 19 is another perspective view of the surgical instrument container with the orthopaedic surgical instrument of FIG. 12 positioned in the lower shell.
Figure 20:
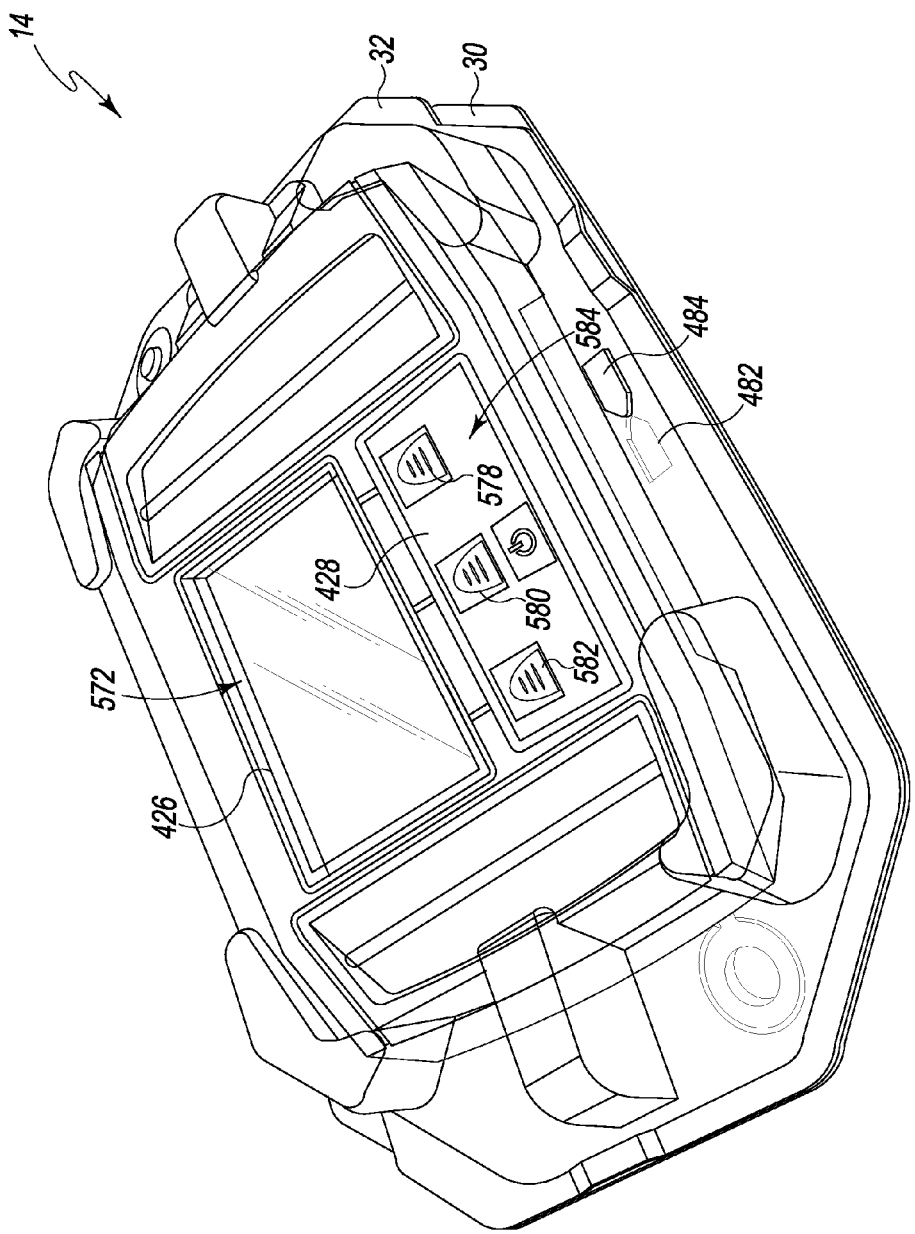
FIG. 20 is a perspective view of the assembled surgical instrument container showing the orthopaedic surgical instrument of FIG. 12 positioned therein.
Figure 21:
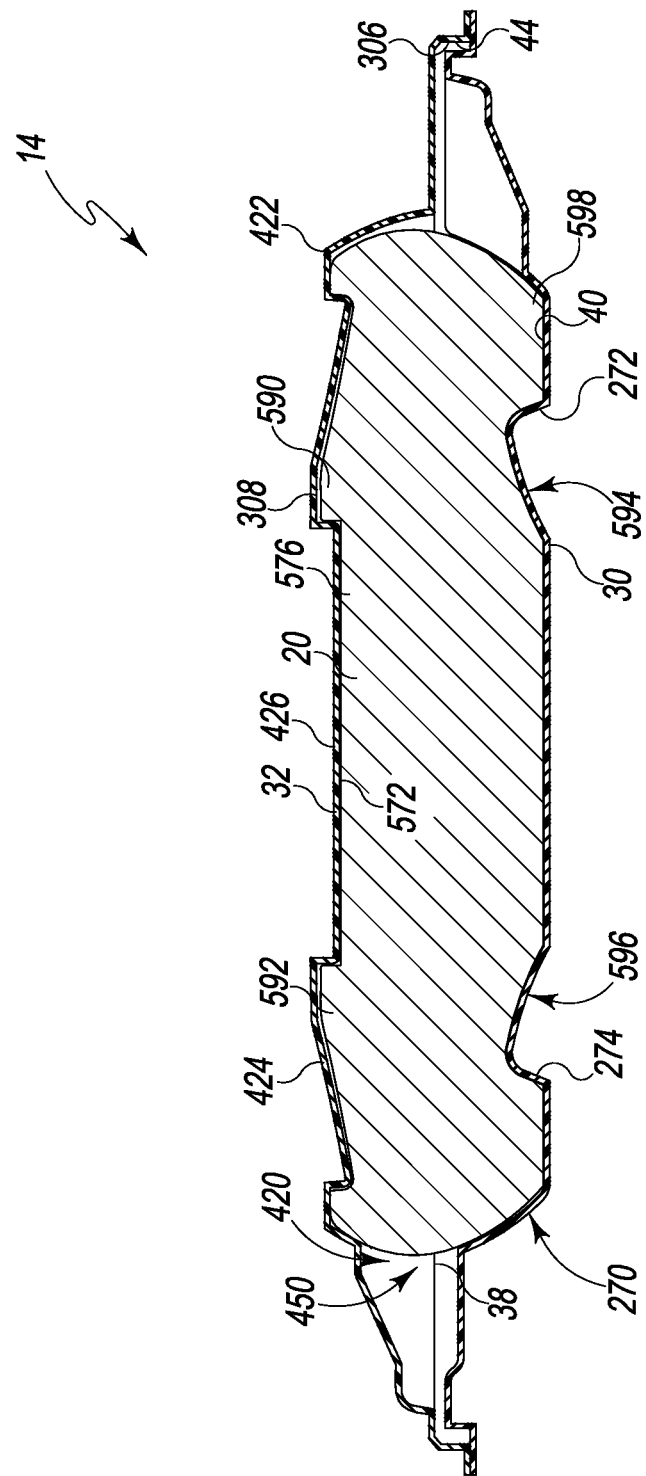
FIG. 21 is a cross-sectional side elevation view of the surgical instrument container assembled as shown in FIG. 20.

Referring now to FIGS. 19-21, the upper shell 32 is positioned in the closed orientation relative to the lower shell 30, and the display module 20 is received in the lower shell 30. When received in the lower shell 30, the lower side 598 of the display module 20 is positioned in the receiving slot 270. As described above, the receiving slot 270 is keyed to match the structure of the lower side 598 of the display module 20. As shown in FIG. 21, the ribs 272, 274 extending from the base wall 42 are received in the grooves 594, 596, respectively, defined in the lower side 598 of the display module 20. Additionally, the rib 588 of the display module 20 is received in the slot 280 defined in the rib 274 of the lower shell 30.

As shown in FIG. 20, the upper shell 32 may be lowered onto the lower shell 30 in the closed orientation when the display module 20 is received therein. As described above, the rim 38 of the lower shell 30 extends through the opening 302 of the upper shell 32, and the outer wall 44 of the lower shell 30 engages the inner wall 306 of the upper shell 32. The compartments 34, 300 of the shells 30, 32 cooperate to define a chamber 450 within the container 14. As described above, no vents are defined in the container 14 such that fluid is prevented from advancing into and out of the chamber 450 in the closed orientation. As shown in FIG. 20, the indicator arrows 484 of the upper shell 32 point toward the indicator arrows 482 of the lower shell 30 while the arrows 482 point toward the arrows 484. As a result, the user is informed that fluid is prevented from advancing into and out of the chamber 450.

As shown in FIG. 21, the receiving slots 270, 420 of the shells 30, 32, respectively, define a receptacle 474 that receives the display module 20. As described above, the slot 420 of the upper shell 32 is keyed to match the structure of the upper side 576 of the display module 20. As shown in FIG. 21, the ribs 422, 424 extending from the base wall 308 are received in the grooves 590, 592, respectively, defined in the upper side 576 of the display module 20. Additionally, the slots 572, 584 of the display module 20 receive the protrusions 426, 428 of the upper shell 32, and the rib 588 of the display module 20 is received in the slot 280 defined in the rib 274 of the lower shell 30. A surgeon or other user is prevented attaching the upper shell 32 in the open orientation when the display module 20 is received in the lower shell 30 due to the matching structure of the slots 572, 584 and the rib 274 of the display module 20, on one hand, and the protrusions 426, 428 and the slot 280 of the upper shell 32, on the other. Thus, when the display module 20 is received in the lower shell 30, the upper shell 32 may be attached to the lower shell 30 in only the closed orientation.

In an orthopaedic surgical procedure, a surgeon may access the buttons 578, 580, 582 of the display module 20 while the display module 20 is positioned in the container 14. As shown in FIG. 20, the surgeon may press on the outer surface 610 of the shell 32 to operate the buttons 578, 580, 582 and control the operation of the sensor module 16 and/or display module 20.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A container for surgical instruments, comprising:
a first shell,
a second shell configured to be coupled to the first shell to define a chamber therebetween, wherein the second shell is configured to be coupled to the first shell in a plurality of orientations including (i) a first orientation in which the first shell and the second shell cooperate to define a vent that permits fluid to advance into and out of the chamber, and (ii) a second orientation in which the first shell and the second shell cooperate to prevent fluid from advancing into and out of the chamber, and
an indicator configured to indicate a selected orientation of the plurality of orientations of the second shell relative to the first shell, the indicator including a first arrow defined in the first shell and a second arrow defined in the second shell, wherein the first arrow and the second arrow cooperate to define (i) a first arrow configuration in which the first arrow and the second arrow point in a first direction when the second shell is coupled to the first shell in the first orientation, and (ii) a second arrow configuration in which the first arrow points in the first direction and the second arrow points in a second direction opposite the first direction when the second shell is coupled to the first shell in the second orientation.

2. The container of claim 1, wherein:
a first passageway is defined in the first shell,
a second passageway is defined in the second shell, and
when the second shell is coupled to the first shell in the first orientation, the first passageway is aligned with the second passageway to define the vent, and when the second shell is coupled to the first shell in the second orientation, the first passageway is spaced apart from the second passageway.

3. The container of claim 2, wherein:
the first shell includes (i) a rim that defines an outward-facing opening, (ii) an inner wall that extends inwardly from the opening to define a compartment in the first shell, and (iii) an outer wall that extends from the rim opposite the inner wall, and
the first passageway is a channel defined in the rim that extends through the inner wall and the outer wall.

4. The container of claim 3, wherein the second shell includes an inner wall that is configured to engage the outer wall of the first shell when the second shell is coupled to the first shell, and the second passageway extends through the inner wall of the second shell.

5. The container of claim 4, wherein:
the first shell includes a flange extending outwardly from the outer wall,
the second shell includes a flange that is engaged with the flange of the first shell when the second shell is coupled to the first shell, and
the second passageway is a channel extending through the inner wall and the flange of the second shell.

6. The container of claim 3, wherein:
the compartment of the first shell is a first compartment,
the second shell includes (i) a rim that defines an outward-facing opening, and (ii) an inner wall that extends inwardly from the opening to define a second compartment in the second shell, and
when the second shell is coupled to the first shell, (i) the inner wall of the second shell engages the outer wall of the first shell, and (ii) the first compartment and the second compartment cooperate to define the chamber.

7. The container of claim 1, wherein when the second shell is coupled to the first shell in the first orientation, the first shell and the second shell cooperate to define a receptacle sized to receive a first orthopaedic surgical instrument of the orthopaedic surgical instruments.

8. The container of claim 7, wherein when the second shell is coupled to the first shell in the first orientation, the first shell and the second shell cooperate to define a second receptacle sized to receive a second orthopaedic surgical instrument of the orthopaedic surgical instruments.

9. The container of claim 1, wherein the vent defined by the first shell and the second shell when the second shell is coupled to the first shell in the first orientation is a plurality of vents that permit fluid to advance into and out of the chamber.

10. A system for use in an orthopaedic surgical procedure, comprising:
an orthopaedic surgical instrument having a first side and a second side,
a first shell defining a first slot sized to receive the first side of the orthopaedic surgical instrument, and
a second shell configured to be coupled to the first shell, the second shell defining a second slot sized to receive the second side of the orthopaedic surgical instrument,
wherein the second shell is configured to be coupled to the first shell in a plurality of orientations including a first orientation in which (i) the first slot and the second slot cooperate to define a receptacle sized to receive the orthopaedic surgical instrument and (ii) fluid is permitted to advance into and out of the receptacle, and
wherein when the orthopaedic surgical instrument is received in the first slot of the first shell and the second shell is in a second orientation of the plurality of orientations, the second shell is configured to engage the orthopaedic surgical instrument such that the second shell is prevented from being coupled to the first shell in the second orientation.

11. The system of claim 10, wherein the first shell includes (i) a rim that defines an outward-facing opening and (ii) an inner wall that extends inwardly from the opening to a base wall, and the inner wall and the base wall define a compartment in the first shell that includes the first slot.

12. The system of claim 11, wherein the first slot of the first shell includes:
a first end defined by (i) a first inner surface of the first shell located in an imaginary plane positioned between the rim and the base wall, and (ii) a curved surface extending upwardly from the first inner surface, and
a second end defined by (i) a second inner surface located in a second imaginary plane positioned between the rim and the base wall, the second inner surface extending parallel to the first inner surface, (ii) a third inner surface located in a third imaginary plane positioned between the rim and the second imaginary plane, and (iii) a fourth inner surface extending obliquely between the second inner surface and the third inner surface.

13. The system of claim of claim 12, wherein the second shell includes (i) a rim that defines an outward-facing opening and (ii) an inner wall that extends inwardly from the opening to a base wall, and the inner wall and the base wall define a compartment in the second shell that includes the second slot.

14. The system of claim 13, wherein the second slot of the second shell includes:
a first end defined by a first inner surface of the second shell, the first inner surface being located in a fourth imaginary plane positioned between the rim and the base wall of the second shell, and
a second end defined by (i) a second inner surface of the second shell, the second inner surface of the second shell being located in a fifth imaginary plane positioned between the rim and the base wall of the second shell, (ii) a third inner surface of the second shell, the third inner surface being located in a sixth imaginary plane positioned between the rim of the second shell and the fifth imaginary plane, and (iii) a fourth inner surface of the second shell extending obliquely between the second inner surface and the third inner surface of the second shell.

15. The system of claim 14, wherein:
when the second shell is coupled to the first shell in the first orientation, the first end of the first slot of the first shell and the first end of the second slot of the second shell are aligned to define a first end of the receptacle, and the second end of the first slot and the second end of the second slot are aligned to define a second end of the receptacle, and
when the second shell is coupled to the first shell in the second orientation, the first end of the first slot is aligned with the second end of the second slot.

16. The system of claim 10, further comprising a second orthopaedic surgical instrument, wherein when the second shell is coupled to the first shell in the second orientation, the first shell and the second shell cooperate to define a second receptacle sized to receive the second orthopaedic surgical instrument.

17. The system of claim 16, wherein when the second shell is coupled to the first shell in the second orientation, fluid is prevented from advancing into and out of the second receptacle.

18. A system for use in an orthopaedic surgical procedure, comprising:
a first orthopaedic surgical instrument,
a second orthopaedic surgical instrument, and
a container comprising:
a first shell including (i) a rim that defines an outward-facing opening, (ii) an inner wall that extends inwardly from the opening to a base wall, the inner wall and the base wall defining a first compartment, and (iii) an outer wall that extends from the rim opposite the inner wall, and
a second shell configured to be coupled to the first shell in a plurality of orientations, the second shell including (i) a rim that defines an outward-facing opening, and (ii) an inner wall that extends inwardly from the opening to a base wall, the inner wall and the base wall of the second shell defining a second compartment,
wherein when the second shell is coupled to the first shell, (i) the inner wall of the second shell engages the outer wall of the first shell, and (ii) the first compartment and the second compartment cooperate to define a chamber in the container, and
wherein the plurality of orientations include (i) a first orientation in which fluid is permitted to advance into and out of the chamber and the chamber includes a first receptacle sized to receive the first orthopaedic surgical instrument, and (ii) a second orientation in which fluid is prevented from advancing into and out of the chamber and the chamber includes a second receptacle sized to receive the second orthopaedic surgical instrument.

19. The system of claim 18, wherein:
the first shell includes a first passageway that extends through the inner wall and the outer wall of the first shell,
when the second shell is coupled to the first shell in the first orientation, the first passageway is aligned with a second passageway of the second shell to permit fluid to advance into and out of the chamber, and
when the second shell is coupled to the first shell in the second orientation, the first passageway is spaced apart from the second passageway to prevent fluid from advancing into and out of the chamber.

20. The system of claim 19, wherein the inner wall of the second shell is positioned over the first passageway of the first shell when the second shell is coupled to the first shell in the second orientation.

21. The system of claim 19, wherein:
the first passageway includes a first channel defined in the rim of the first shell, and
the second passageway includes a second channel defined in the second shell.

* * * * *